(12) United States Patent
McKernon et al.

(10) Patent No.: US 10,660,691 B2
(45) Date of Patent: May 26, 2020

(54) MULTIPLE USE SUBASSEMBLY WITH INTEGRATED FLUID DELIVERY SYSTEM FOR USE WITH SINGLE OR DUAL-LUMEN PERISTALTIC TUBING

(71) Applicant: ANGIODYNAMICS, INC., Latham, NY (US)

(72) Inventors: Jennifer McKernon, South Glens Falls, NY (US); Scott Wheeler, Queensbury, NY (US); Ryan Bean, Westminster, MA (US); Wesley Joe, Fremont, CA (US)

(73) Assignee: AngioDynamics, Inc., Latham, NY (US)

( * ) Notice: Subject to any disclaimer, the term of this patent is extended or adjusted under 35 U.S.C. 154(b) by 656 days.

(21) Appl. No.: 15/288,422

(22) Filed: Oct. 7, 2016

(65) Prior Publication Data

US 2017/0156783 A1 Jun. 8, 2017

Related U.S. Application Data

(60) Provisional application No. 62/238,299, filed on Oct. 7, 2015.

(51) Int. Cl.
*A61B 18/12* (2006.01)
*A61N 1/32* (2006.01)
(Continued)

(52) U.S. Cl.
CPC .......... *A61B 18/1206* (2013.01); *A61N 1/327* (2013.01); *A61B 18/1815* (2013.01);
(Continued)

(58) Field of Classification Search
CPC ............ A61B 18/1206; A61B 18/1482; A61B 18/1402; A61B 18/1492;
(Continued)

(56) References Cited

U.S. PATENT DOCUMENTS 4,676,258 A 6/1987 Inokuchi et al.
4,810,963 A 3/1989 Blake-Coleman et al.
(Continued)

FOREIGN PATENT DOCUMENTS

EP 0378132 A2 7/1990
EP 2008604 A2 7/1990
(Continued)

OTHER PUBLICATIONS

Bruners, et al, A Newly Developed Perfused Umbrella Electrode for RF Ablation: An Ex Vivo Evaluation Study in Bovine Liver, Cardiovasc Intervent Radiol, 2007, pp. 992-998.
(Continued)

*Primary Examiner* — Michael F Peffley
(74) *Attorney, Agent, or Firm* — Peter J. Flora, Esq.

(57) ABSTRACT

The present disclosure relates to systems and methods for regulating, maintaining and/or controlling the temperature of fluids and tissues during therapeutic or ablative tissue treatment applications. In particular, the present disclosure relates to a multi-purpose subassembly that is easy to use, supports all infusion and fluid-cooled ablation systems, and readily and reliably accepts a variety of tubing designs to decrease preparation time and minimize user error during setup and use.

20 Claims, 21 Drawing Sheets

(51) Int. Cl.
*A61B 18/00* (2006.01)
*A61B 18/18* (2006.01)

(52) U.S. Cl.
CPC .............. *A61B 2018/00023* (2013.01); *A61B 2018/00029* (2013.01); *A61B 2018/00035* (2013.01); *A61B 2018/00166* (2013.01); *A61B 2018/00577* (2013.01); *A61B 2018/00613* (2013.01); *A61B 2018/00791* (2013.01); *A61B 2018/00863* (2013.01)

(58) Field of Classification Search
CPC ........... A61B 2218/00577; A61B 2018/00791; A61B 2018/00029; A61B 2018/00291; A61B 2018/00744; A61B 2018/00714; A61B 2018/00863; A61B 2018/00011; A61B 2018/1472; A61B 2018/00583; A61B 2018/00005; A61B 2018/00166; A61B 2218/002; A61B 2218/007
See application file for complete search history.

(56) References Cited

U.S. PATENT DOCUMENTS

| | | | |
|---|---|---|---|
| 4,891,483 A | 1/1990 | Kikuchi et al. | |
| 4,907,601 A | 3/1990 | Frick | |
| 4,946,793 A | 8/1990 | Marshall, III | |
| 5,098,843 A | 3/1992 | Calvin | |
| 5,173,158 A | 12/1992 | Schmukler | |
| 5,283,194 A | 2/1994 | Schmukler | |
| 5,328,451 A | 7/1994 | Davis et al. | |
| 5,348,554 A * | 9/1994 | Imran ............... | A61B 18/1492 606/41 |
| 5,439,440 A | 8/1995 | Hofmann | |
| 5,647,871 A * | 7/1997 | Levine ............... | A61B 18/1402 606/45 |
| 5,720,921 A | 2/1998 | Meserol | |
| 5,735,847 A | 4/1998 | Gough et al. | |
| 5,810,804 A | 9/1998 | Gough et al. | |
| 5,983,131 A | 11/1999 | Weaver et al. | |
| 6,027,502 A | 2/2000 | Desai | |
| 6,059,780 A | 5/2000 | Gough et al. | |
| 6,066,134 A | 5/2000 | Eggers et al. | |
| 6,090,105 A | 7/2000 | Zepeda et al. | |
| 6,090,106 A | 7/2000 | Goble et al. | |
| 6,102,885 A | 8/2000 | Bass | |
| 6,132,419 A | 10/2000 | Hofmann | |
| 6,134,476 A | 10/2000 | Arndt et al. | |
| 6,347,247 B1 | 2/2002 | Dev et al. | |
| RE37,704 E * | 5/2002 | Eshel .................... | A61B 18/08 604/113 |
| 6,436,072 B1 | 8/2002 | Kullas et al. | |
| 6,500,173 B2 | 12/2002 | Underwood et al. | |
| 6,613,211 B1 | 9/2003 | McCormick et al. | |
| 6,627,421 B1 | 9/2003 | Unger et al. | |
| 6,653,091 B1 | 11/2003 | Dunn et al. | |
| 6,673,070 B2 | 1/2004 | Edwards et al. | |
| 6,682,501 B1 | 1/2004 | Nelson et al. | |
| 6,697,670 B2 | 2/2004 | Chomenky et al. | |
| 6,712,811 B2 | 3/2004 | Underwood et al. | |
| 6,770,070 B1 | 8/2004 | Balbierz | |
| 6,795,728 B2 | 9/2004 | Chornenky et al. | |
| 6,865,416 B2 | 3/2005 | Dev et al. | |
| 6,869,430 B2 | 3/2005 | Balbierz et al. | |
| 6,962,587 B2 | 11/2005 | Johnson et al. | |
| 6,972,014 B2 | 12/2005 | Eum et al. | |
| 6,994,706 B2 | 2/2006 | Chornenky et al. | |
| 7,063,698 B2 | 6/2006 | Whayne et al. | |
| 7,211,083 B2 | 5/2007 | Chornenky et al. | |
| 7,267,676 B2 | 9/2007 | Chornenky et al. | |
| 7,344,533 B2 | 3/2008 | Pearson et al. | |
| 7,488,292 B2 | 2/2009 | Adachi | |
| 7,553,309 B2 | 6/2009 | Buysse et al. | |
| 7,699,842 B2 | 4/2010 | Buysse et al. | |
| 7,763,018 B2 | 7/2010 | DeCarlo et al. | |
| 7,771,401 B2 | 8/2010 | Hekmat et al. | |
| 7,879,031 B2 | 2/2011 | Peterson | |
| 8,052,604 B2 | 11/2011 | Lau et al. | |
| 8,059,059 B2 | 11/2011 | Bonn | |
| 8,062,290 B2 | 11/2011 | Buysse et al. | |
| 8,182,477 B2 | 5/2012 | Orszulak et al. | |
| 8,187,270 B2 | 5/2012 | Auth et al. | |
| 8,292,880 B2 | 10/2012 | Prakash et al. | |
| 8,346,370 B2 | 1/2013 | Haley et al. | |
| 8,361,062 B2 | 1/2013 | Bonn | |
| 8,394,078 B2 * | 3/2013 | Torrance ........ | A61B 17/320758 604/22 |
| 8,394,092 B2 | 3/2013 | Brannan | |
| 8,398,626 B2 | 3/2013 | Buysse et al. | |
| 8,401,668 B2 | 3/2013 | Deem et al. | |
| 8,406,894 B2 | 3/2013 | Johnson et al. | |
| 8,417,328 B2 | 4/2013 | Sarfaty et al. | |
| 8,437,845 B2 | 5/2013 | Sarfaty et al. | |
| 8,439,907 B2 | 5/2013 | Auth et al. | |
| 8,469,951 B2 | 6/2013 | Ben-Haim et al. | |
| 8,512,329 B2 | 8/2013 | Paulus | |
| 8,535,302 B2 | 9/2013 | Ben-Haim et al. | |
| 8,551,088 B2 | 10/2013 | Falkenstein et al. | |
| 8,562,598 B2 | 10/2013 | Falkenstein et al. | |
| 8,568,401 B2 | 10/2013 | Brannan | |
| 8,568,411 B2 | 10/2013 | Falkenstein et al. | |
| 8,579,894 B2 | 11/2013 | Falkenstein et al. | |
| 8,608,739 B2 | 12/2013 | Sartor et al. | |
| 8,668,688 B2 | 3/2014 | Rusin | |
| 8,672,937 B2 | 3/2014 | DeCarlo et al. | |
| 8,688,228 B2 | 4/2014 | Johnson et al. | |
| 8,740,893 B2 | 6/2014 | Shiu et al. | |
| 8,745,854 B2 | 6/2014 | Bonn | |
| 8,825,176 B2 | 9/2014 | Johnson et al. | |
| 8,845,559 B2 | 9/2014 | Darlington et al. | |
| 8,865,076 B2 | 10/2014 | Sarfaty et al. | |
| 8,894,641 B2 | 11/2014 | Brannan | |
| 8,915,910 B2 | 12/2014 | Falkenstein et al. | |
| 8,926,605 B2 | 1/2015 | McCarthy et al. | |
| 8,932,284 B2 | 1/2015 | McCarthy et al. | |
| 8,945,111 B2 | 2/2015 | Brannan et al. | |
| 8,954,161 B2 | 2/2015 | McCarthy et al. | |
| 8,961,506 B2 | 2/2015 | McCarthy et al. | |
| 8,965,536 B2 | 2/2015 | Bonn et al. | |
| 9,014,814 B2 | 4/2015 | McCarthy et al. | |
| 9,028,477 B2 | 5/2015 | Ben-Haim et al. | |
| 9,050,449 B2 | 6/2015 | Darlington et al. | |
| 9,095,350 B2 | 8/2015 | Condie et al. | |
| 9,113,888 B2 | 8/2015 | Orszulak et al. | |
| 9,113,924 B2 | 8/2015 | Brannan et al. | |
| 9,113,932 B1 | 8/2015 | Willyard et al. | |
| 9,149,331 B2 | 10/2015 | Deem et al. | |
| 9,888,956 B2 * | 2/2018 | Model ................ | A61B 18/1815 |
| 2002/0077627 A1 | 6/2002 | Johnson et al. | |
| 2002/0077676 A1 | 6/2002 | Schroeppel et al. | |
| 2002/0193831 A1 | 12/2002 | Smith | |
| 2003/0009110 A1 | 1/2003 | Tu et al. | |
| 2003/0014047 A1 | 1/2003 | Woloszko et al. | |
| 2003/0060856 A1 | 3/2003 | Chornenky et al. | |
| 2003/0088189 A1 | 5/2003 | Tu et al. | |
| 2003/0130711 A1 | 7/2003 | Pearson et al. | |
| 2003/0170898 A1 | 9/2003 | Gundersen et al. | |
| 2003/0225360 A1 | 12/2003 | Eppstein et al. | |
| 2004/0059328 A1 | 3/2004 | Daniel et al. | |
| 2004/0146877 A1 | 7/2004 | Diss et al. | |
| 2004/0153057 A1 | 8/2004 | Davison | |
| 2004/0204679 A1 | 10/2004 | Visconti et al. | |
| 2004/0243107 A1 | 12/2004 | Macoviak et al. | |
| 2004/0267340 A1 | 12/2004 | Cioanta et al. | |
| 2005/0015081 A1 | 1/2005 | Turovskiy et al. | |
| 2005/0033276 A1 | 2/2005 | Adachi | |
| 2005/0043726 A1 | 2/2005 | McHale et al. | |
| 2005/0165393 A1 | 7/2005 | Eppstein | |
| 2005/0261672 A1 | 11/2005 | Deem et al. | |
| 2005/0288730 A1 | 12/2005 | Deem et al. | |
| 2006/0079883 A1 | 4/2006 | Elmouelhi et al. | |
| 2006/0106379 A1 | 5/2006 | O'Brien et al. | |
| 2006/0212078 A1 | 9/2006 | Demarais et al. | |

(56) References Cited

U.S. PATENT DOCUMENTS

| | | |
|---|---|---|
| 2006/0217703 A1 | 9/2006 | Chornenky et al. |
| 2006/0293734 A1 | 12/2006 | Scott et al. |
| 2007/0078453 A1 | 4/2007 | Johnson et al. |
| 2007/0156136 A1 | 7/2007 | Godara et al. |
| 2007/0203551 A1 | 8/2007 | Cronin et al. |
| 2008/0039790 A1* | 2/2008 | Hasebe .............. A61B 18/04 604/113 |
| 2008/0275436 A1 | 11/2008 | Cronin et al. |
| 2008/0294155 A1 | 11/2008 | Cronin |
| 2009/0036773 A1 | 2/2009 | Lau et al. |
| 2009/0118725 A1 | 5/2009 | Auth et al. |
| 2009/0118729 A1 | 5/2009 | Auth et al. |
| 2009/0295674 A1 | 12/2009 | Bonn |
| 2010/0082022 A1 | 4/2010 | Haley et al. |
| 2010/0106047 A1 | 4/2010 | Sarfaty et al. |
| 2010/0121173 A1 | 5/2010 | Sarfaty et al. |
| 2011/0098695 A1 | 4/2011 | Brannan |
| 2011/0112531 A1 | 5/2011 | Landis et al. |
| 2011/0118721 A1 | 5/2011 | Brannan |
| 2011/0208180 A1 | 8/2011 | Brannan |
| 2012/0150172 A1 | 6/2012 | Ortiz et al. |
| 2013/0072858 A1 | 3/2013 | Watson et al. |
| 2013/0296679 A1 | 11/2013 | Condie et al. |
| 2014/0081255 A1 | 3/2014 | Johnson et al. |
| 2014/0207133 A1 | 7/2014 | Model et al. |

FOREIGN PATENT DOCUMENTS

| | | |
|---|---|---|
| EP | 2286754 | 7/1990 |
| EP | 2299540 | 7/1990 |
| GB | 2415630 A | 1/2006 |
| GB | 2457299 A | 8/2009 |
| JP | 2011511538 | 8/2009 |
| WO | WO9639531 A1 | 12/1996 |
| WO | WO0020554 A1 | 4/2000 |
| WO | WO2004037341 A2 | 5/2004 |
| WO | WO2006002943 A1 | 1/2006 |
| WO | WO2011042720 | 1/2006 |
| WO | WO2012006533 A1 | 1/2012 |
| WO | WO2015110938 | 1/2012 |

OTHER PUBLICATIONS

Dulucq, et al, Virtually Bloodless Laparoscopic Liver Resection of Recurrent Hepatoma With a New Laparoscopic Sealer Device, Surg Laparosc Endoc Percutan Tech, 2007, pp. 413-415.

Recaldini, Percutaneous Sonographically Guided RF Ablation of Medium-Sized Fibroids: Feasibility Study, AJR:189, 2007, pp. 1303-1306.

Lee, et al, Multiple-Electrode RF Ablation of in Vivo Porcine Liver, Investigative Radiology, pp. 676-683.

Park, et al, Prognostic Factors Influencing the Development of an Iatrogenic Pneumothorax for CT-Guided RF Ablation of Upper Renal Tumor, Acta Radiologica, 2008, pp. 1200-1206.

Gervais, et al, Society of Interventional Radiology Position Statement on Percutaneous RF Ablation for the Treatment of Liver Tumors, 2009, J Vasc Interv Radiol, pp. 3-8.

Thanos, Image-Guided RF Ablation of a Pancreatic Tumor with a New Triple Spiral-Shaped Electrode, Cardiovasc Intervent Radiol, 2010, pp. 215-218.

Carrafiello, et al, Ultrasound-Guided RF Thermal Ablation of Uterine Fibroids: Medium-Term Follow-Up, Cardiovasc Intervent Radiol, 2010, pp. 113-119.

Cha et al, RF Ablation Using a New Type of Interally Cooled Electrode With an Adjustable Active Tip: An Experimental Study in Ex Vivo Bovine and In Vivo Porcine Livers, European Journal of Radiology, 2011, pp. 516-521.

Majid, An Overview of Image-Guided Percutaneous Ablation of Renal Tumors, Semin Intervent Radiol 2010, pp. 261-267.

Carmi, et al, Combination Percutaneous and Intraarterial Therapy for the Treatment of Hepatocullular Carcinoma: A Review, Semin Intervent Radiol 2010, pp. 296-301.

Howenstein, et al, Complications of RF Ablation of Hepatic, Pulmonary, and Renal Neoplasms, Semin Intervent Radiol 2010, pp. 285-295.

Dupuy, et al, Current Status of Thermal Ablation Treatments for Lung Malignancies, Semin Intervent Radiol 2010, pp. 268-275.

Saldanha, et al, Current Tumor Ablation Technologies: Basic Science and Device Review, Semin Intervent Radiol 2010, pp. 247-254.

Kurup, et al, Image-Guided Percutaneous Ablation of Bone and Soft Tissue Tumors, Semin Intervent Radiol 2010, pp. 276-284.

McWilliams, et al, Image-Guided tumor Ablation: Emerging Technologies and Future Directions, Semin Intervent Radiol 2010, pp. 302-313.

McCarley, Percutaneous Ablation of Hepatic Tumors, Semin Intervent Radiol 2010, pp. 255-260.

DeBenedectis, et al, Utility of Iodinated Contrast Medium in Hydrodissection Fluid when Performing Renal Tumor Ablation, J Vasc Interv Radiol 2010, pp. 745-747.

McCall, NanoKnife, Liposomal Doxorubicin Show Efficacy Against Liver Cancer, European Congress of Radiology 2011.

Organ, Electrophysiologic Principles of RF Lesion Making, Int. Symp. Radiofrequency Lesion Making Procedures, 1976, pp. 69-76.

Onik, et al, Sonographic Monitoring of Hepatic Cryosurgery in an Experimental Animal Model, American Roentgen Ray Society, 1985, pp. 1043-1047.

Foster, et al, Production of Prostatic Lesions in Canines Using Transrectally Administered High-Intensity Focused Ultrasound, Eur Urol 1993, pp. 330-336.

Foster, et al, High-Intensity Focused Ultrasound in the Treatment of Prostatic Disease, Eur Urol 1993, pp. 29-33.

Lorentze, The Loop Electrode: In Vivo Evaluation of a Device for Ultrasound-Guided Interstitial Tissue Ablation Using RF Electrosurgery, Acad Radiol, pp. 219-224.

Lorentze, A Cooled Needle Electrode for RF Tissue Ablation: Thermodynamic Aspects of Improved Performance Compared with Conventional Needle Design, Acad Radiol, pp. 556-563.

Zlotta, et al, Possible Mechanisms of Action of Transurethral Needle Ablation of the Prostate on Benign Prostatic Hyperplasia Symptoms: A Neurohistochemical Study, Journal of Urology.

Lorentze, et al, RF Tissue Ablation with a Cooled Needle in Vitro: Ultrasonography, Dose Response and Lesion Temperature, Acad Radiol, pp. 292-297.

Naslund, Transurethral Needle Ablation of the Prostate, Urology 1997, pp. 167-172.

Issa, et al, The TUNA PRocedure for BPH: Review of the Technology, Infections in Urology.

Maybody, An Overview of Image-Guided Percutaneous Ablation of Renal Tumors, Seminars in Interventional Radiology/vol. 27, No. 3, 2010, pp. 261-267.

Carmi, et al, Combination Percutaneous and Intraarterial Therapy for the Treatment of Hepatocellular Carcinoma: A Review, Semin Intervent Radiol 2010, 27:296-301.

Saldanha, et al, Current Tumor Ablation Technologies: Basic Science and Device Review, Semin Intervent Radiol 2010, 27:247-254.

Kurup, et al, Image-Guided Percutaneous Ablation of Bone and soft Tissue Tumors, Semin Intervent Radiol 2010, 27:276-284.

Mccarley, et al, Percutaneous Ablation of Hepatic Tumors, Semin Intervent Radiol 2010, 27: 255-260.

International Search Report PCT-GB-04-002620 ISR, dated Jan. 10, 2004.

International Search Report PCT-EP-05-007103 WOSA, dated Feb. 1, 2007.

International Search Report PCT-GB-99-01398 WOSA, dated Feb. 2, 2000.

International Search Report PCT-EP-06-012144 IPRP, dated Feb. 5, 2008.

International Search Report PCT-EP-05-007553 IPRP, dated Feb. 11, 2006.

International Search Report PCT-GB-94-01565 IPER, dated Feb. 11, 1995.

International Search Report PCT-GB-10-051625 ISR, dated Mar. 5, 2011.

(56) References Cited

OTHER PUBLICATIONS

International Search Report PCT-EP-06-012144 ISR, dated Mar. 7, 2007.
International Search Report PCT-GB-99-01398 ISR, dated Mar. 9, 1999.
International Search Report PCT-GB-99-01400 ISR, dated Mar. 9, 1999.
International Search Report PCT-GB-11-051735 WOSA, dated Apr. 5, 2013.
International Search Report PCT-EP-05-007553 ISR, dated Apr. 10, 2005.
International Search Report PCT-GB-10-051625 WOSA, dated Jun. 4, 2012.
International Search Report PCT-GB-11-051735 IPRP, dated Jul. 5, 2013.
International Search Report PCT-GB-99-01398 IPER, dated Jul. 8, 2000.
International Search Report PCT-EP-05-007103 IPRP, dated Jan. 9, 2007.
International Search Report 09155664 ESR, dated Jun. 9, 2009.
International Search Report PCT-GB-09-050113 IPRP, Aug. 10, 2010.
International Search Report PCT-GB-10-051625 IPRP, dated Apr. 11, 2012.
International Search Report PCT-GB-99-001398 ISR, dated Nov. 11, 1999.
International Search Report PCT-GB-99-001400 ISR, dated Nov. 11, 1999.
International Search Report PCT-EP-05-007103 ISR, dated Jan. 12, 2006.
International Search Report PCT-GB-03-04082 IPER, dated Nov. 12, 2004.
International Search Report PCT-GB-11-051735 ISR, dated Dec. 15, 2011.
International Search Report 04815540 SESR, dated Jan. 21, 2010.
International Search Report PCT-GB-00-00682 IPRP, dated May 21, 2001.
International Search Report PCT-GB-04-002620 IPRP, dated Jul. 21, 2005.
International Search Report PCT-GB-03-004082 ISR, dated Apr. 22, 2004.
International Search Report PCT-GB-00-00682 ISR, dated May 24, 2000.
International Search Report PCT-GB-09-050113 ISR, dated May 25, 2009.
International Search Report PCT-US-04-043477 IPRP, dated Jun. 26, 2006.
International Search Report PCT-US-04-043477 ISR, dated Aug. 26, 2005.
International Search Report, PCT-GB-94-01565 ISR, dated Nov. 28, 1994.
Rubinskey, Cryosurgery, Annu. Rev. Biomed. Eng. 2000, 02: pp. 157-187.
Carson, et al, BPH Management Strategies, Urology Times, vol. 29, Supplemental 1.
Naslund, et al, Cost-effectiveness of Minimally Invasive Treatments and Transurethral Resection in Benign Prostatic Hyperplasia, AUA National Meeting, 2001, pp. 1213.
Zlotta et al, Long-term Evaluation of Transurethral NEedle Ablation of the Prostate for Treatment of Benign Prostatic Hyperlasia: Clinial Outcomes After 5 Years, AUA National Meeting, 2001, pp. 1024.
ViaMed, Inc. Office TUNA System clinical trail summary, 2001.
Chandrasekar, et al, Transurethral Needle Ablation of the Prostate—A Prospective Study, Six Year Follow Up, AUA National Meeting, 2001, pp. 1210.
ViaMed, Inc. Office TUNA System Patient Brochure, 2001.
Lee, RadioFrequency Ablation of Uterine Leiomyomata: A New Minimally Invasive Hysterectomy Alernative, Tuesday Papers, vol. 99, No. 4 (Supplement), 2002, pp. 9S.
Chang, Finite Elemenet Analysis of Hepatic RF Ablation Probes using Temperature-Dependent Electical Conductivity, BioMedical Engineering OnLine 2003, 2:12.
Schmedt, et al, Evaluation of Endovenous RF Ablation and Laser Therapy with Endoluminal Optical Coherence Tomography in an Ex Vivo Model, The Society for Vascular Surgery 2007, pp. 1047-1058.
Knight, et al, Direct Imaging of Transvenous RF Cardiac Ablation Using a Streerable Fiberoptic Infrared Endoscope, Heart Shythm Society, 2005, pp. 1116-1121.

\* cited by examiner

MULTIPLE USE SUBASSEMBLY WITH INTEGRATED FLUID DELIVERY SYSTEM FOR USE WITH SINGLE OR DUAL-LUMEN PERISTALTIC TUBING

CROSS REFERENCE TO RELATED APPLICATIONS

The present application claims benefit of U.S. Provisional Patent Application No. 62/238,299 filed Oct. 7, 2015 and is hereby incorporated by reference.

FIELD

The present disclosure relates generally to systems and methods for therapeutic or ablative tissue treatment applications. Specifically, the present disclosure relates to systems and methods for regulating, maintaining and/or controlling the temperature of fluids and tissues during such applications.

BACKGROUND

Using ablation technology to treat human tissue is currently known in the art. Ablation technology, such as radiofrequency (RF), microwave, and irreversible electroporation (IRE)—including thermal IRE and non-thermal IRE—are well-known for their applicability in treatment, coagulation and/or targeted ablation or treatment of tissue in the human body. During procedures using such technology, a treatment probe, commonly either an electrode or antenna, is typically advanced into the patient laproscopically, percutaneously or through an open surgical incision until the target tissue is reached. Once properly positioned at the target site, energy is transferred to the probe. The type, amount, and range of energy delivered to the probe varies and depends on the specific treatment modality. During transmission of treatment energy to the target tissue, the outer surface of the probe and/or the cables transmitting the energy may reach high temperatures specifically when the treatment energy is in the form of either RF or microwave energy. When exposed to such elevated temperatures, the treatment site, as well as the surrounding tissue, may be unintentionally heated beyond the desired treatment parameters or treatment zone. Cooling fluid may be circulated through the ablation system to remove excess heat from the probe and/or cable, prevent device malfunctioning and/or avoid unintended harm to the user or patient. To remove excess heat generated by the system, the cooling fluid may be circulated through the ablation system. Commonly, peristaltic pumps, or other similar type pumps known in the art, are used together with inflow and outflow tubing to circulate the cooling fluid. Typically, the cooling system is such that the cooling fluid travels to the probe through inflow tubing that passes through a peristaltic pump head, and returns through outflow tubing that bypasses the peristaltic pump head. Examples devices and apparatuses for thermal treatment of tissues and their operation are described in U.S Patent Application Publication Nos. 20130197504 and 20140207133 and U.S. Pat. Nos. 8,540,710 and 9,084,619, the contents of which are incorporated herein by reference as though set forth in full.

In general, such treatment probes as discussed above fall within one of the following categories: 1) infusion probes, 2) fluid-cooled probes and 3) standard probes (i.e., no cooling/infusion).

Infusion probes introduce saline, or other electrically conductive fluids, into the target site to increase the size of the tissue treatment zone. The infused saline increases tissue conductivity, allowing the energy to propagate farther into the target tissue to provide faster procedure times and larger treatment zones. The saline also minimizes tissue desiccation and charring by conducting energy away from the probe tip where it is most concentrated. This is important since charred and/or desiccated tissue tends to act as an insulator that hinders efficient ablation of the surrounding tissue. Because overheating is generally not an issue with infusion systems, the saline is delivered through a single-lumen tube at a much lower flow rate than required for a fluid-cooled ablation probe. Other infusion devices, such as IRE delivery probes deliver therapeutic agents (e.g., drug-coated nanoparticles, growth factors, etc.) into the target tissue, or require infusion of temperature controlling fluid (such as saline) to prevent unwanted sparking between electrodes that may short out the system and possibly harm the patient.

Fluid-cooled ablation probes include a closed fluid channel through which saline or gas circulates to dissipate heat away from the probe tip where the treatment energy is concentrated. As with infusion probes, the circulating coolant prevents tissue desiccation and/or charring that would interfere with ablation of the target tissue. Since the circulating coolant does not enter the tissue there is no "enhanced conduction" of the treatment energy.

The different flow rates and tubing designs required for infusion and fluid-cooled ablation systems often require specifically designed peristaltic pumps that are not amenable for multi-purpose use. Peristaltic pumps for infusion ablation systems may not be robust enough to support the higher fluid flow rates required for fluid-cooled ablation systems. For example, a typical infusion ablation system may require infusion fluid to be delivered at a flow rate of 0.05-0.7 ml/min, while a typical fluid-cooled ablation system may require coolant to be circulated at a flow rate in excess of 80 ml/min. Additionally, peristaltic pumps for fluid-cooled ablation systems include complex routing paths for inflow vs. outflow tubing, which complicates setup and increases the likelihood of user error.

There is a need for a multi-purpose subassembly that is easy to use, supports all infusion and fluid-cooled ablation systems and readily and reliably accepts a variety of tubing designs to decrease preparation time and minimize user error during setup and use.

SUMMARY

The present disclosure relates generally to a multiple-use subassembly that supports infusion and fluid-cooled ablation systems for the treatment or ablation of tissue.

In one aspect, the present disclosure relates to a system for ablating a treatment site, comprising: a multiple-use subassembly comprising a housing that includes an energy source and a pump motor; an integrated pump head may be connected to the pump motor; and an ablation probe may be electrically connected to the energy source by one or more wires. The integrated pump head may include a roller assembly configured to support peristalsis. The system may further include a fluid source fluidly connected to the ablation probe by a length of tubing which passes through the integrated pump head. The integrated pump head may be configured to flow a fluid from the fluid source to the ablation probe through the length of tubing. The tubing may include single-lumen peristaltic tubing, multiple-lumen peristaltic tubing or multi-lumen tubing. The fluid source may include a cooling fluid. In addition, or alternatively, the fluid source may include an electrically conductive fluid, including, for example, sterile saline. The energy source may be capable of generating radiofrequency energy, microwave energy and/or electroporation energy. The multi-lumen tubing may include an inflow lumen and an outflow lumen, wherein the inflow lumen is configured to close when compressed by a roller of the roller assembly and the outflow lumen is configured to remain open when compressed by a roller of the roller assembly. The fluid may flow from the fluid source to the ablation probe through the inflow lumen and return to the fluid source through the outflow lumen. In one embodiment, the fluid may flow through the multi-lumen tubing at a flow rate of at least 60 ml/min; preferably at least 80 ml/min, more preferably at least 100 ml/min and even more preferably at least 120 ml/min. The single-lumen tubing may include an inflow lumen configured to close when compressed by a roller of the roller assembly. The fluid may flow from the fluid source to the ablation probe through the inflow lumen of the single-lumen tubing. The fluid may flow through the single lumen tubing at a flow rate of approximately 0.05 ml/min to approximately 0.7 ml/min.

In another aspect, the present disclosure relates to dual-lumen tube comprising: an inflow tube comprising an inflow lumen; and an outflow tube comprising an outflow lumen, wherein the inflow lumen is configured to fully close within a peristaltic pump and the outflow lumen is configured to remain open with a peristaltic pump. One or more insulated wire(s) may extend along the length of the multi-lumen tubing between the inflow and outflow tubes.

In one embodiment, the inflow and outflow tubes may include substantially identical outer diameters (e.g., at least 0.125 inch; at least 0.150 inch; at least 0.175 inch; at least 0.200 inch; at least 0.225 inch; at least 0.250 inch; at least 0.275 inch; at least 0.300 inch). The outer diameter of the inflow tube is equal to the inner diameter of the inflow lumen plus the wall thickness of the of the inflow tube. Similarly, the outer diameter of the outflow tube is equal to the inner diameter of the outflow lumen plus the wall thickness of the outflow tube. While the inflow and outflow tubes of the multi-lumen tubing may include a variety of different internal and external dimensions, the wall thickness of the inflow tube generally remains greater (i.e., larger) than the wall thickness of the outflow tube, and the inner diameter of the inflow lumen generally remains less (i.e., smaller) than the inner diameter of the outflow lumen. By way of non-limiting example, the inner diameter of the inflow lumen may be at least 0.050 inch; at least 0.060 inch; at least 0.070 inch; at least 0.080 inch; at least 0.090 inch. By way of non-limiting example, the wall of the inflow tube may include a thickness of at least 0.050 inch; at least 0.060 inch; at least 0.070 inch; at least 0.080 inch; at least 0.090 inch; at least 0.100 inch; at least 0.110 inch; at least 0.120 inch; at least 0.130 inch; at least 0.140 inch; at least 0.150 inch. By way of non-limiting example, the inner diameter of the outflow lumen may be at least 0.100 inch; at least 0.110 inch; at least 0.120 inch; at least 0.130 inch; at least 0.140 inch; at least 0.150 inch; at least 0.175 inch; at least 0.200 inch. By way of non-limiting example, the wall of the outflow tube may include a thickness of at least 0.010 inch; at least 0.020 inch; at least 0.030 inch; at least 0.040 inch.

In another embodiment, the outer diameter of the inflow tube may be larger than the outer diameter of the outflow tube. The outer diameter of the inflow tube is equal to the inner diameter of the inflow lumen plus the wall thickness of the of the inflow tube (e.g., at least 0.125 inch; at least 0.150 inch; at least 0.175 inch; at least 0.200 inch; at least 0.225 inch; at least 0.250 inch; at least 0.275 inch; at least 0.300 inch). Similarly, the outer diameter of the outflow tube is equal to the inner diameter of the outflow lumen plus the wall thickness of the outflow tube (e.g., at least 0.050 inch; at least 0.075 inch; at least 0.100 inch). While the inflow and outflow tubes of the multi-lumen tubing may include a variety of different internal and external dimensions, the wall thickness of the inflow tube generally remains greater (i.e., larger) than the wall thickness of the outflow tube, and the inner diameter of the inflow lumen generally remains substantially the same as the inner diameter of the outflow lumen. By way of non-limiting example, the inner diameter of the inflow and outflow lumens may be at least 0.050 inch; at least 0.060 inch; at least 0.070 inch; at least 0.080 inch; at least 0.090 inch. By way of non-limiting example, the wall of the inflow tube may include a thickness of at least 0.050 inch; at least 0.060 inch; at least 0.070 inch; at least 0.080 inch; at least 0.090 inch; at least 0.100 inch; at least 0.110 inch; at least 0.120 inch; at least 0.130 inch; at least 0.140 inch; at least 0.150 inch. By way of example, the wall of the outflow tube may include a thickness of at least 0.010 inch; at least 0.020 inch; at least 0.030 inch; at least 0.040 inch.

BRIEF DESCRIPTION OF THE DRAWINGS

Non-limiting embodiments of the present disclosure will be described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one or ordinary skill in the art to which the disclosure belongs.

Figure 1:
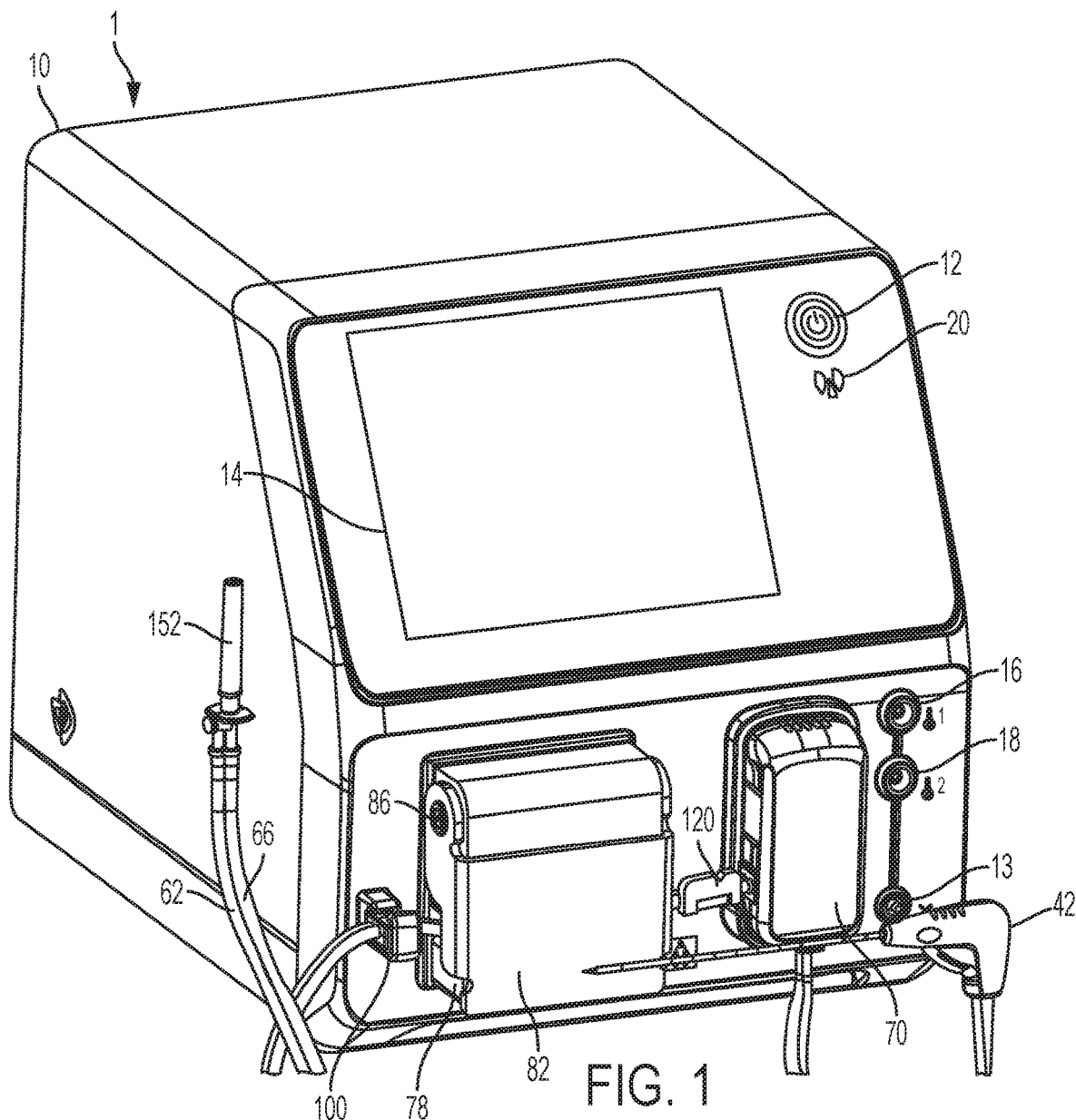
FIG. 1 depicts a front view of a multiple-use subassembly, according to one embodiment of the present disclosure.

As illustrated in FIG. 1, the multiple-use subassembly 1 of the present disclosure may include a housing 10, a power button 12, a user interface screen 14, a first set of probe connection points 16, a second set of probe connection points 18, a power indicator 20, a pump connection 22 and a third probe connection points 13. The pump connection 22 may include a drive shaft, a peristaltic pump or a piston style pump as commonly known in the art. The housing 10 may be made of metal or other suitable material capable of withstanding repeated and multiple uses, normal wear and tear and may be easily cleaned. The user interface screen 14 may include a touch screen computer that displays a GUI operating system designed to help guide the user through preparation and operation of the system. The first 16, second 18, and third 13 probe connection points may be either an RF, IRE or microwave energy connection point as commonly known in the art. Alternatively, any of the probe connection points may be used to electrically connect to grounding pads (not shown), as known in the art. Although only three probe connections are shown it is within the conception of this invention to include additional probe connections depending on the number of probes required during use. The power indicator 20 may include an LED or visual identification source to indicate that power has activated the system.

Also illustrated in FIG. 1., the single-use subassembly of the present disclosure may include a probe 42, tubing for delivering fluid from the fluid source 52 to the probe 42, a fluid spike 152 for gaining access to the fluid source, and a flow sensor 120 for giving accurate measurements of flow rate. The probe in the present disclosure is capable of delivering energy including, but not limited to microwave, RF, ultrasound, irreversible electroporation, and reversible electroporation.

Figure 2:
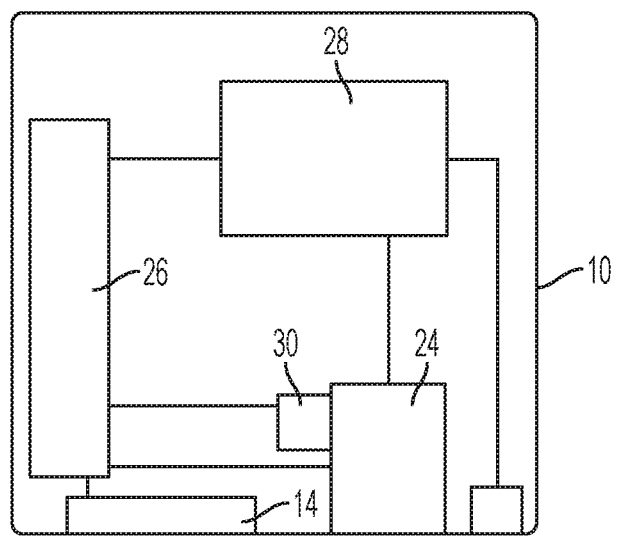
FIG. 2 depicts a partial top cross-sectional view of the housing of the multiple-use subassembly of FIG. 1.

FIG. 2 provides a schematic top cross-section view of the housing 10, which further includes a pump motor 24, a power source 26, an energy source 28 (e.g., energy generator), a circuit board 30 and an electrical connector (not shown). In one embodiment, the energy generator may provide microwave energy. In another embodiment, the energy generator may provide RF energy. In a third embodiment, the energy generator may provide either reversible or irreversible electroporation energy. In a fourth embodiment, the energy generator may provide a combination of RF, microwave, and either reversible and/or irreversible electroporation energy. The power source 26 is connected to a power cord (not shown) and is capable of generating the power required to run the entire multiple-use subassembly, including the interface screen 14, the pump motor 24, the circuit board 30 and the energy source 28. The pump connection 22 (FIG. 1) may be connected to the pump motor 24, as known in the art. The pump motor 24 may be securely attached to the housing 10 such that at least a portion of the pump connection 22 extends beyond the housing 10 to receive the roller assembly 76 (not shown) of the pump head 70 (not shown), discussed below. The pump motor 24 may include any stepper motor, brushed motor or brushless motor as known in the art. In one embodiment, the pump motor may be a stepper motor that is directly connected to the pump connection. Alternatively, if a brushed or brushless motor (not shown) is used, then such motor may be connected to a gear box (not shown) within the housing.

The circuit board 30 may include automatically set preprogrammed treatment parameters including, but not limited to, specific power settings, algorithms and flow rates depending on the type of ablation system connected to the multiple-use subassembly. To provide repeatable and reliable procedure endpoints, the circuit board 30 may be controlled by a user interface configured to monitor the temperature at the probe tip in real-time, and automatically adjust the treatment energy delivered to the ablation zone to maintain optimal temperatures during the ablation procedure. The energy source 28 may be configured to provide the electrical energy required for a variety of ablation systems, including, but not limited to, microwave ablation, RF ablation and thermal or non-thermal irreversible electroporation (IRE). For example, a 2.45 GHz microwave generator may supply electrosurgical RF energy for partial or complete coagulation and ablation of soft tissue. Energy is transferred from the energy source 28 to the microwave connection 13 or probe connection 18 connection points (FIG. 1) of the multiple-use subassembly.

As described herein, the multiple use subassembly 1 may be compatible for use with a variety of fluid-cooled or infusion ablation systems. Depending on the type of ablation system, unique or dedicated probe connection points 18 may be required within the housing 10 of the multiple-use subassembly. For example, one embodiment may include a multiple-use subassembly with dedicated standard RF pin-type electrical connection points. Another embodiment may include a multiple-use subassembly with dedicated microwave electrical connection points. Yet another embodiment may include a multiple-use subassembly with dedicated high voltage electrical connection points (not shown). Alternatively, in another embodiment, the housing of the multiple-use subassembly may include a single universal electrical connection point configured to deliver RF, microwave or IRE ablation energy to the selected ablation probe. The circuit board 30 may be configured to recognize the specific type of ablation system probe as it is plugged into its respective connection point, and automatically set a pre-loaded computer driven software tissue protocol. The type of ablation probe used with the multiple-use subassembly may vary depending on the medical procedure being performed.

It is a common problem known in the art that the insulated wire(s) transmitting microwave or RF energy from the probe connection points to the ablation probe may conduct heat and cause an increase in temperature that could burn skin and/or tissue or cause other unwanted/unintended damage to the patient and/or user. In one embodiment, the present disclosure provides a cooling system in which the insulated wire(s) are cooled and remain at a safe temperature by circulating a cooling fluid throughout the ablation delivery device using multi-lumen tubing. In addition to cooling the ablation probe the circulating fluid absorbs the heat generated by the wire(s), thereby cooling the wire(s) to prevent thermal injury to the user and/or patient. A minimum flow rate is required to maintain the cooling fluid at a temperature below the maximum permissible skin contact temperature of approximately 48° C. For example, prior to starting the ablation procedure, the temperature of the cooling fluid within the fluid source may range from approximately 5° C. (i.e., chilled) to approximately 22° C. (i.e., room temperature). This temperature may increase to approximately 30° C. during the ablation procedure as the fluid circulates through the system. Assuming a maximum temperature of 30° C., the cooling fluid must circulate through the multi-lumen tubing at a flow rate of approximately 80 ml/min to maintain the coolant below the maximum permissible temperature of 48° C. It is also a common problem known in the art that transmitting IRE energy at certain pulse parameters may cause sparking between electrodes that leads to unwanted complications during a procedure. One possible solution to this problem is the infusion or circulation of temperature controlled fluid through the IRE probe. The advantage of such a design is that the probe does not increase in temperature that would result in unwanted sparking that may short out the system.

Figure 3A:
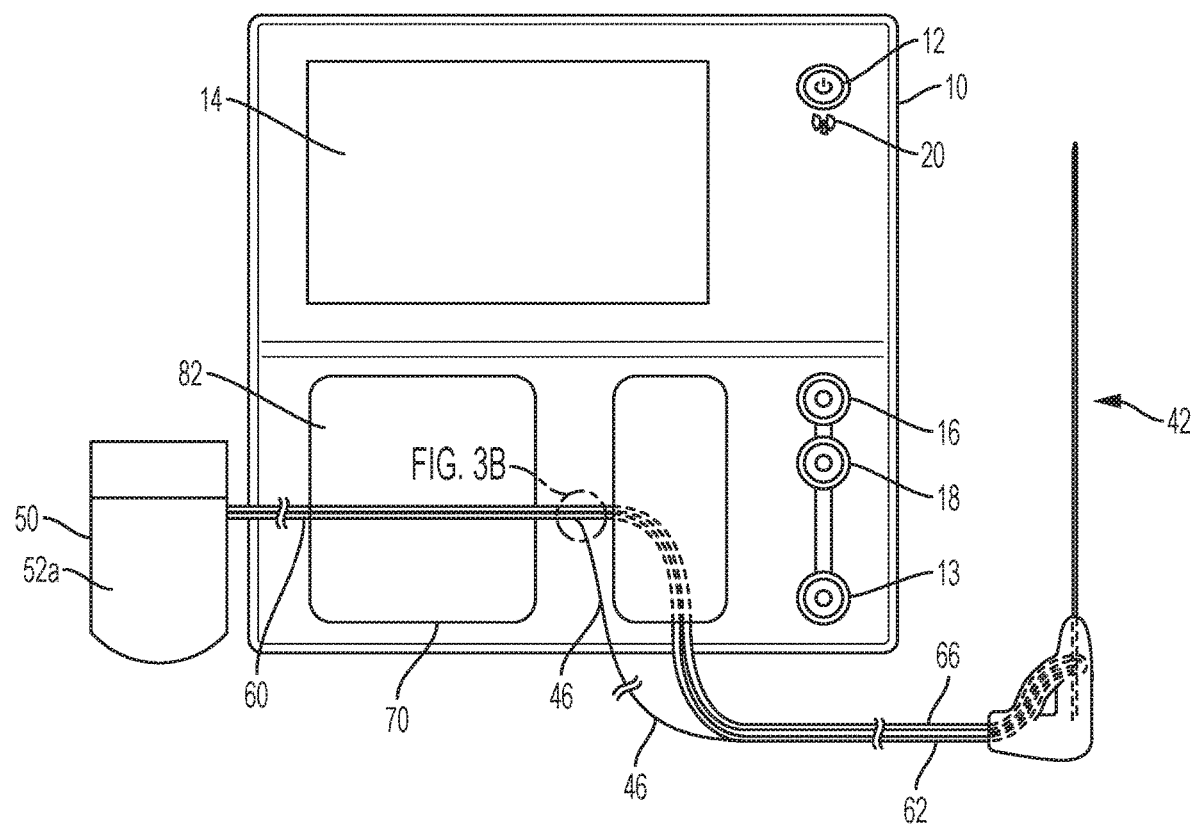
FIGS. 3A-B depict a partial front view of a multiple-use subassembly that includes an integrated pump head configured to circulate cooling fluid from a fluid source to a fluid-cooled ablation probe, according to one embodiment of the present disclosure.
Figure 3B:
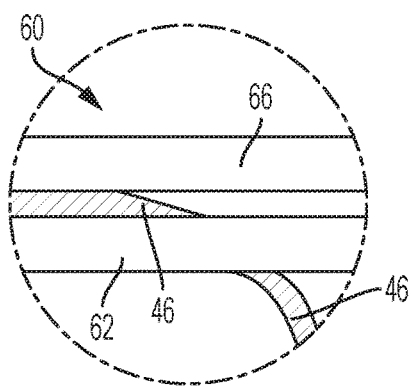
Figure 3C:
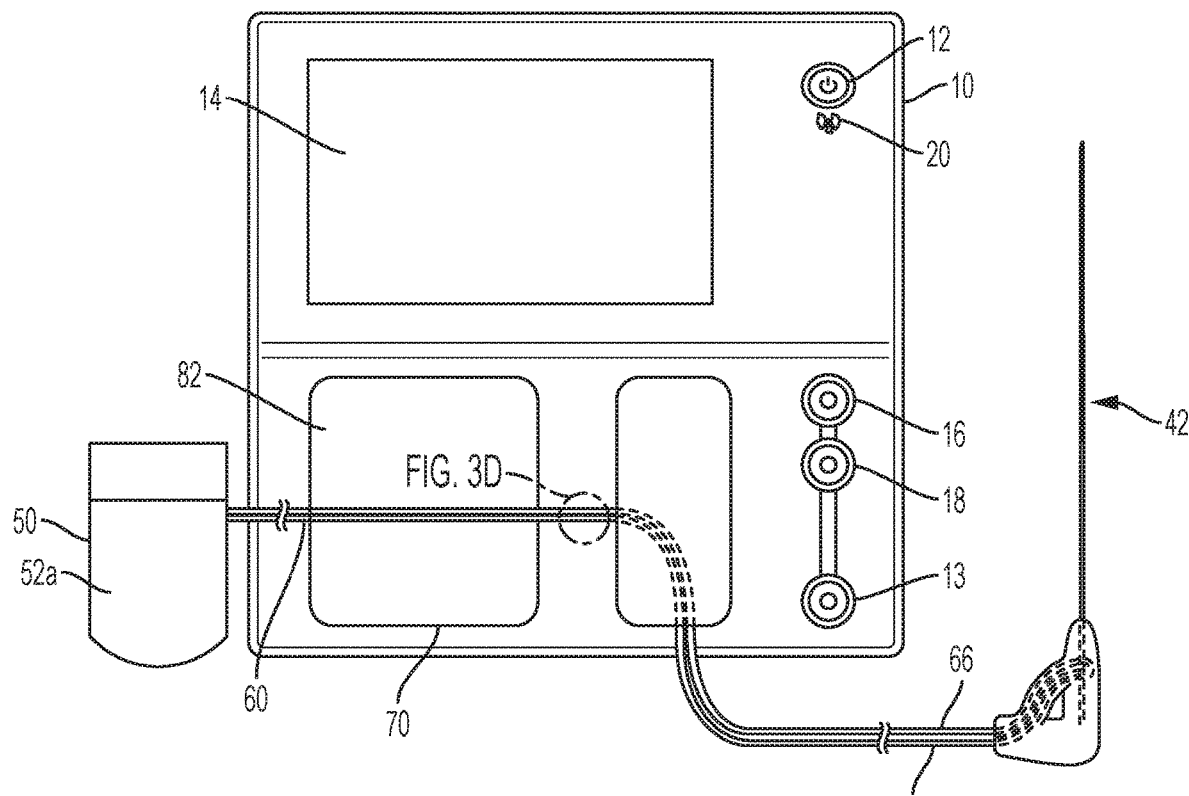
FIGS. 3C-D depict a partial front view of a multiple-use subassembly that includes an integrated pump head configured to circulate cooling fluid from a fluid source to a fluid-cooled ablation probe, according to another embodiment of the present disclosure.
Figure 3D:
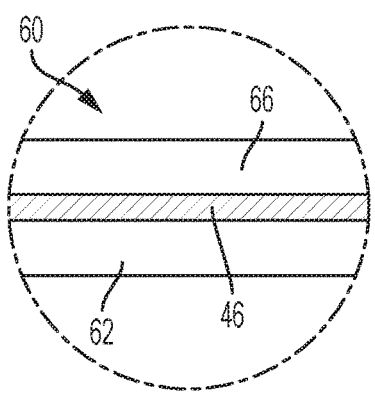
Figure 3E:
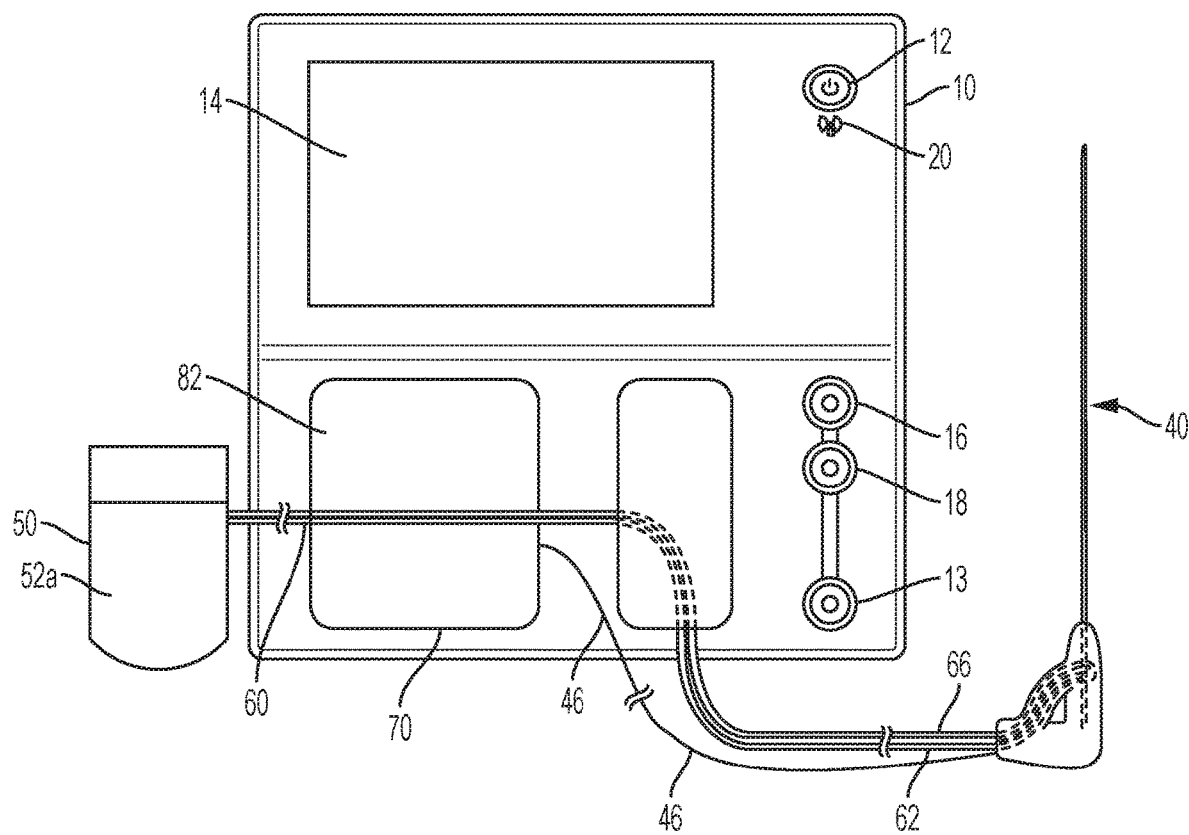
FIG. 3E depicts a partial front view of a multiple-use subassembly that includes an integrated pump head configured to circulate infusion fluid from a fluid source to an infusion ablation probe, according to yet another embodiment of the present disclosure.

Referring to FIG. 3A, in one embodiment the multiple-use subassembly of FIG. 1 may include an integrated peristaltic pump head 70 configured to circulate a fluid 52a, such as sterile saline at or below room temperature, from a fluid source 50 to an ablation probe 42 through a multi-lumen tubing 60 (i.e., dual-lumen fluid source line). The multi-lumen tubing 60 may be dual-lumen tubing as shown, but more than two lumens are within the conception of this invention. The multi-lumen tubing 60 may include an inflow tube 62 for flowing fluid 52a from the fluid source 50 to the fluid-cooled ablation probe 42, and an outflow (i.e., return) tube 66 for returning the fluid 52a to the fluid source 50 for re-cooling and/or re-circulation. Alternatively, the outflow tube 66 may transfer the fluid 52a to a waste container (not shown). The fluid-cooled ablation probe 42 may be electrically connected to the probe connection points 18 by one or more insulated wires 46. As depicted in the enlarged view of FIG. 3B, at least a portion of the insulated wire(s) 46 coaxially extend along or next to the inflow 62 and outflow 66 tubes of the multi-lumen tubing 60. In one embodiment, the insulated wire(s) 46 may split from the dual-lumen 60 tubing prior to entering the pump head 70. In another embodiment, as shown in FIGS. 3C-D, the wire(s) 46 may remain within multi-lumen tubing 60 along its entire length as it passes through the pump head 70 to the fluid-cooled ablation probe 42. Referring to FIG. 3E, in yet another embodiment, the multiple-use subassembly may be used with an infusion ablation system to flow infusion fluid 52b from the fluid source 50 to an infusion ablation probe 40 through a dual-lumen tubing 61.

Conventional fluid-cooled ablation systems require separate inflow and outflow tubes to circulate cooling fluid. The inflow tube typically passes through the peristaltic pump, as described above, but the cooling fluid returns to the fluid source through a separate outflow tube that bypasses the peristaltic pump. This requires the user to be cognizant of the inflow and outflow tubing as the latter is specifically routed through the system to avoid the peristaltic pump. Although dual-lumen peristaltic tubing is known in the art, the lumens of both tubes are subject to peristalsis and are therefore limited to unidirectional fluid flow. The ability to support unidirectional flow through two (or more) tubes may be beneficial for certain applications, including, for example infusion ablation systems with multiple (e.g., 5 or more) infusion tines each connected to a separate inflow tube. However, currently available multi-lumen tubing, for example, as shown in prior art FIGS. 4A and 4B, cannot support bi-directional fluid flow (i.e., fluid circulation) without re-routing the outflow tube to bypass the peristaltic pump. If both the inflow and outflow tubing were to be routed through the peristaltic pump, both tubes would completely collapse when subjected to the pressure from the roller assembly 76 of the pump head 70, also shown in prior art FIGS. 4A and 4B. The multi-lumen tubing of the present disclosure is unlike previously described multi-lumen tubing in that it includes an inflow tube configured for peristalsis, and an outflow tube positioned within the pump that is not subject to peristalsis because it never fully collapses within the peristaltic pump head.

Figure 5A:
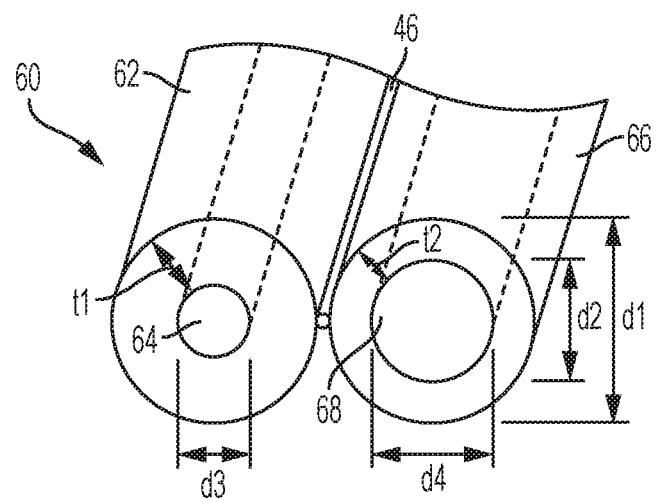
FIGS. 5A-B depict a cross-sectional isometric view of multi-lumen tubing that includes inflow and outflow tubes in the uncompressed (FIG. 5A) and compressed (FIG. 5B) configurations, according to one embodiment of the present disclosure.

Referring to FIG. 5A, in one embodiment, the multi-lumen tubing 60 of the present disclosure includes an inflow tube 62 and an outflow tube 66 with a substantially identical outer diameter $d_1$ (e.g., approximately 0.188 in.-0.199 in.). The inflow tube 62 includes an inflow lumen 64 with an inner diameter $d_3$ (e.g., approximately 0.079 in.) and a wall thickness $t_1$ (e.g., approximately 0.050-0.060 in.). The outflow tube 66 includes an outflow lumen 68 with an inner diameter $d_4$ (e.g., approximately 0.125 in.) and a wall thickness $t_2$ (e.g., approximately 0.031-0.032 in.). An insulated wire(s) 46 may extend along the length of the multi-lumen tubing 60 between the inflow 62 and outflow 66 tubes. It should be appreciated that these tubing dimensions are provided by way of non-limiting example. A variety of tubing dimensions are contemplated by the present disclosure wherein: 1) the outer diameter $d_1$ of the inflow tube 62 is equal to the inner diameter $d_3$ of the inflow lumen plus the wall thickness $t_1$ of the inflow tube; 2) the outer diameter $d_1$ of the outflow tube 66 is equal to the inner diameter $d_4$ of the outflow lumen plus the wall thickness $t_2$ of the outflow tube; 3) the wall thickness $t_1$ of the inflow tube is greater than the wall thickness $t_2$ of the outflow tube and 4) the inner diameter $d_3$ of the inflow lumen is less than the inner diameter $d_4$ of the outflow lumen.

Figure 5B:
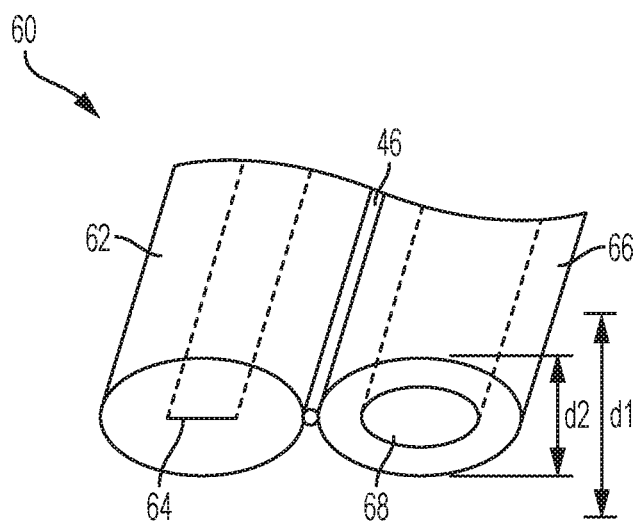

Referring to FIG. 5B, the roller assembly (discussed below) may compress the inflow 62 and outflow 66 tubes from the first outer diameter $d_1$ to a second outer diameter $d_2$ (e.g., approximately 0.100 in.). The thicker wall $t_1$ of the inflow tube 62 causes the inflow lumen 64 to completely collapse, thereby pumping cooling fluid from the fluid source to the ablation probe. By contrast, the thinner wall $t_2$ of the outflow tube 66 does not cause the outflow lumen 68 to completely collapse, thereby maintaining a continuously open lumen through which the cooling fluid may return from the ablation probe to the fluid source. Accordingly, the tubing configuration shown in FIGS. 5A and 5B also provides the ability to support bi-directional flow through the inflow and outflow tubes, both of which can be positioned within the pump head.

Figure 6A:
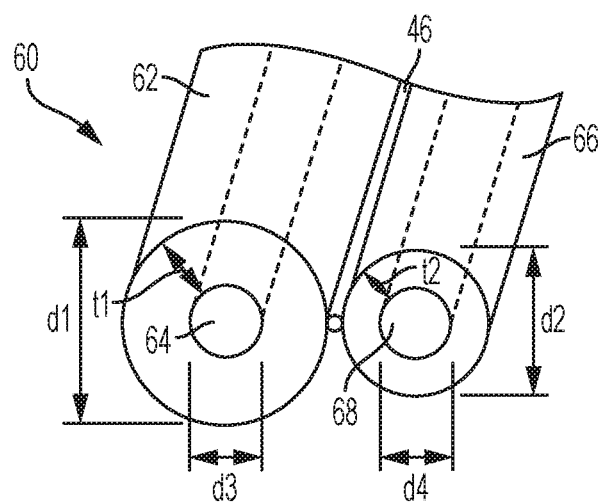
FIGS. 6A-B depict a cross sectional isometric view of multi-lumen tubing that includes inflow and outflow tubes in uncompressed (FIG. 6A) and compressed (FIG. 6B) configurations, according to another embodiment of the present disclosure.

Referring to FIG. 6A, in another embodiment, the multi-lumen tubing 60 may include an inflow tube 62 with an outer diameter $d_1$ (e.g., 0.188 in.-0.199 in.) and outflow tube 66 with smaller outer diameter $d_2$ (e.g., approximately 0.100 in.). The inflow tube 62 includes an inflow lumen 64 with an inner diameter $d_3$ (e.g., approximately 0.079 in.) and a wall thickness $t_1$ (e.g., approximately 0.060 in.). The outflow tube 66 includes an outflow lumen 68 with an inner diameter $d_4$ that is substantially the same as the inner diameter $d_3$ of the inflow lumen 64 (e.g., approximately 0.079 in.) and a wall thickness $t_2$ (e.g., approximately 0.031 in.). An insulated wire(s) 46 may extend along the length of the multi-lumen tubing 60 between the inflow 62 and outflow 66 tubes. It should be appreciated that these tubing dimensions are provided by way of non-limiting example. A variety of tubing dimensions are contemplated by the present disclosure wherein: 1) the outer diameter $d_1$ of the inflow tube 62 is equal to the inner diameter $d_3$ of the inflow lumen plus the wall thickness $t_1$ of the outflow tube; 2) the outer diameter $d_1$ of the outflow tube 66 is equal to the inner diameter $d_4$ of the outflow lumen plus the wall thickness $t_2$ of the outflow tube; 3) the wall thickness $t_1$ of the inflow tube is greater than the wall thickness $t_2$ of the outflow tube and 4) the inner diameter $d_3$ of the inflow lumen is substantially the same as the inner diameter $d_4$ of the outflow lumen.

Figure 6B:
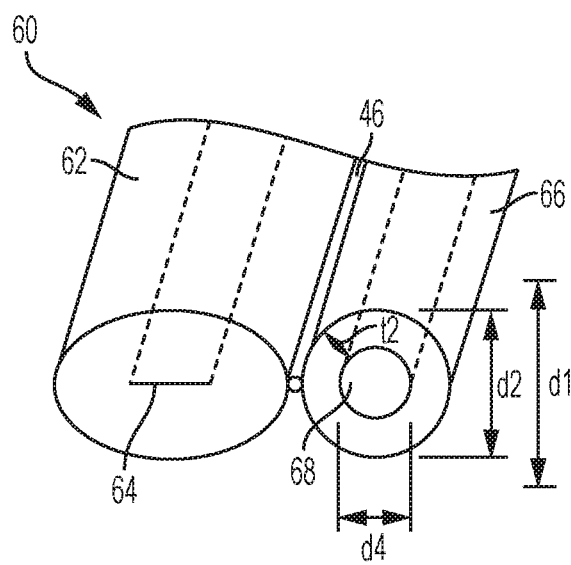

Referring to FIG. 6B, the roller assembly (discussed below) may compress the inflow tube 62 to a second outer diameter $d_2$ (e.g., 0.100 in.) that forces the inflow lumen 64 to completely collapse, thereby pumping cooling fluid from the fluid source to the ablation probe. The smaller outer diameter $d_2$ (e.g., 0.100 in.) of the outflow tube 66 is not substantially compressed by the roller assembly, thereby maintaining an open outflow lumen 68 through which fluid may return from the ablation probe to the fluid source. Accordingly, the tubing configuration shown in FIGS. 6A and 6B also provides the ability to support bi-directional flow through the inflow and outflow tubes, both of which can be positioned within the pump head.

As will be understood by those of skill in the art, the multi-lumen tubing described herein may be made from a variety of polymer-based materials of different durometer (i.e., hardness or compressibility), thickness and/or pliability. Non-limiting examples of such materials may include silicone, synthetic or natural rubbers, nylon, vinyl, polyurethanes and polyethylenes, among others. Each tube of the multi-lumen tubing may be simultaneously formed from the same material by a dual-extrusion process. Alternatively, each tube of the multi-lumen tubing may be formed from the same or different materials by a separate single-extrusion process and then bonded together. A wide assortment of reinforcing material may be incorporated within the inflow and/or outflow tube during the extrusion process to increase its durability and/or flexibility. By way of non-limiting example, the tubing may be reinforced with a braided, woven, spiral and/or knitted arrangement of fibers, steel cord or other suitable structures. The wire(s) 46 extending within multi-lumen tubing 60 may be co-extruded along with the inflow 62 and outflow 66 tubes. Alternatively, the multi-lumen tubing 60 may be co-extruded to include a third smaller lumen between the inflow 62 and outflow 66 tubes. The wire(s) 46 may then be inserted into the third lumen after the tubing has been formed.

In yet another embodiment, the flow of fluid in the inflow and outflow tubes are controlled by varying the durometer of the tubes. For example, the inflow tube may be made of a material with a softer durometer and as such will compress more readily, thereby more easily collapsing the lumen of the inflow tube. Conversely, the outflow tube may be made of a material with a harder durometer that will not compress as easily as the lower durometer material of the inflow tube, thereby allowing the lumen of the outflow tube to remain open when placed under the same pressure as the inflow tube. It is also appreciated that the dimensions of the inflow tubing and outflow tubing can remain the same, but the difference in hardness of the material used on the outflow tubing can have the same effect as the embodiment of FIGS. 5A/B and 6A/B. Another advantage of this embodiment would be ease of manufacture of the tubing, as the dimensions of both the inflow and outflow tubing would be identical.

Referring to FIG. 7A-14, one embodiment of the pump head 70 is shown. The pump head 70 may include a body 72, a face plate 74, a roller assembly 76, an occlusion bed 78 and a front cover 82. The roller assembly 76 is housed within the body 72 and is configured to receive the pump connection 22 of the multiple-use subassembly (FIG. 1). Although the roller assembly 76 includes six rollers 77 (e.g., FIG. 7A), it will be appreciated that the number of rollers may range from two rollers up to nine rollers, or more. The occlusion bed 78 may include a bottom surface 80 comprising a concave portion 80a flanked by substantially planar portions 80b. The concave portion 80a includes a substantially hemispherical shape configured to align with the corresponding convex profile of the roller assembly 76. As discussed in greater detail below, the occlusion bed 78 is pivotally coupled to the body 72 of the pump head 70 by a first hinge 84, and to the front cover 82 by a second hinge 86.

Figure 7A:
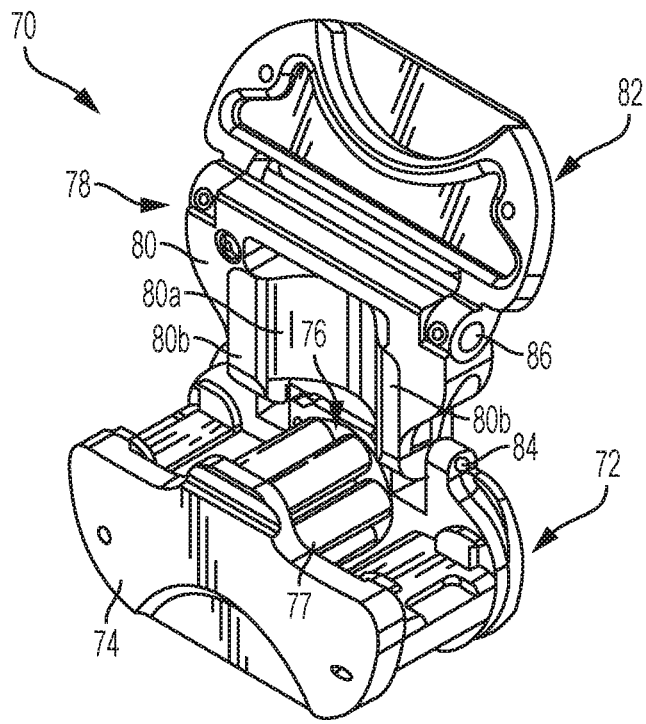
FIGS. 7A-B depict an isometric view of a pump assembly in a fully open configuration (FIG. 7A) and with a length of multi-lumen tubing positioned across the roller assembly (FIG. 7B), according to one embodiment of the present disclosure.
Figure 7B:
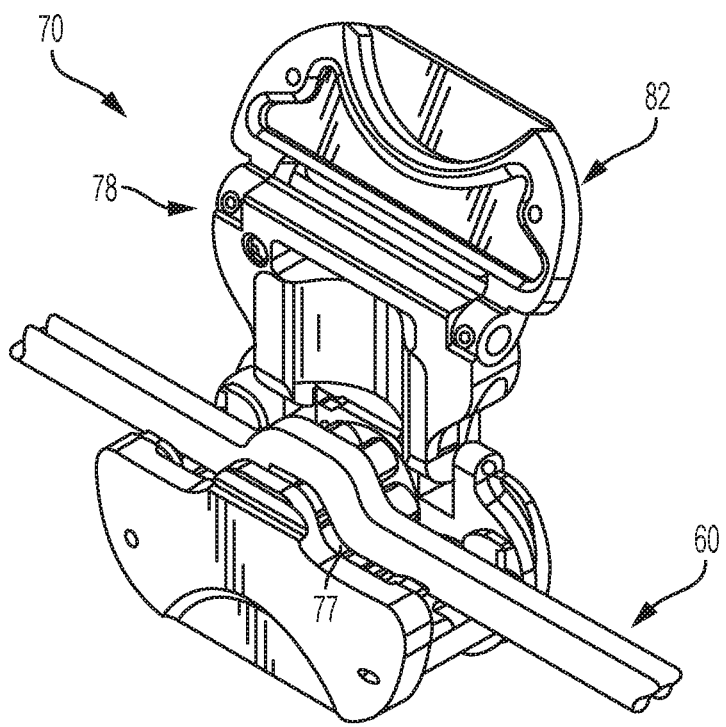

Referring to FIG. 7B, the pump head 70 provides an easy-to-load layout when the occlusion bed 78 and front cover 82 are in the fully open configuration, such that single (not shown) or multi-lumen tubing 60 may be placed across the roller assembly 76 without obstruction.

Figure 4A:
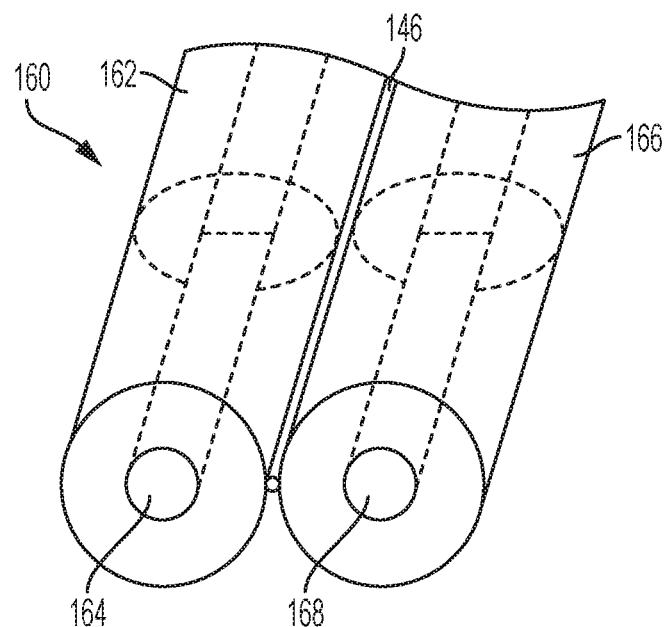
FIGS. 4A-B depict a cross-sectional isometric view of a prior art multi-lumen tubing in the uncompressed (FIG. 4A) and compressed (FIG. 4B) configurations.
Figure 4B:
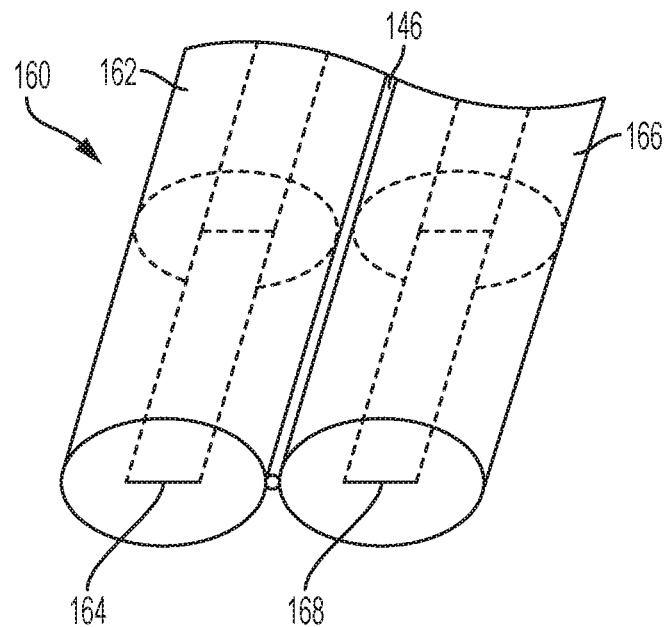
Figure 8A:
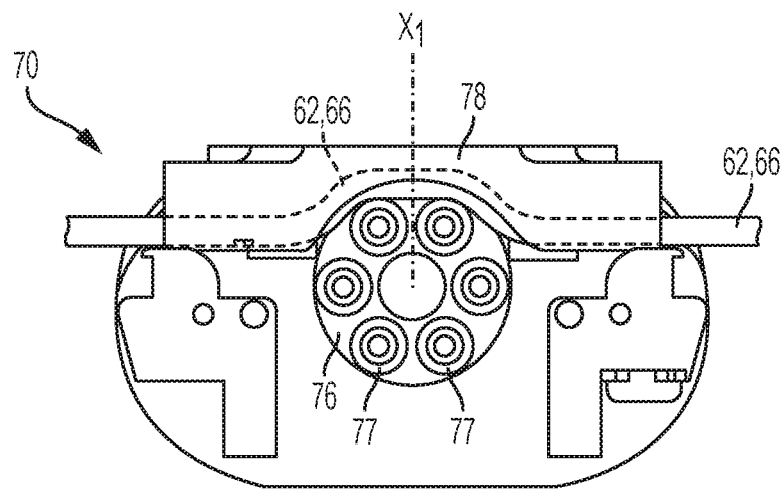
FIGS. 8A-D depict side (FIGS. 8A, 8C) and front (FIGS. 8B, 8D) cross-sectional views of the multi-lumen tubing of FIGS. 5A-B within a pump assembly in a fully closed configuration, according to one embodiment of the present disclosure.
Figure 8B:
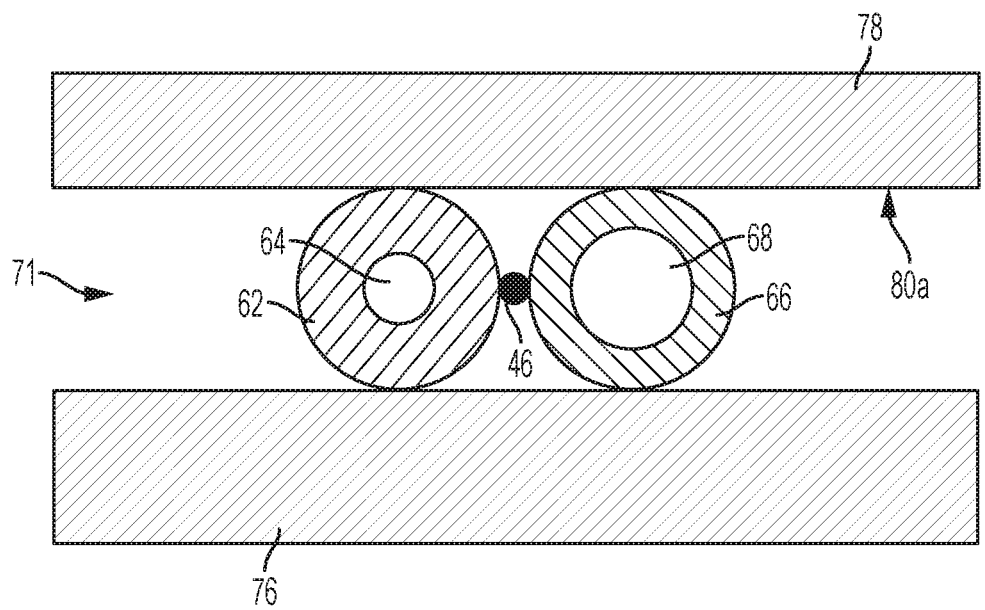
Figure 8C:
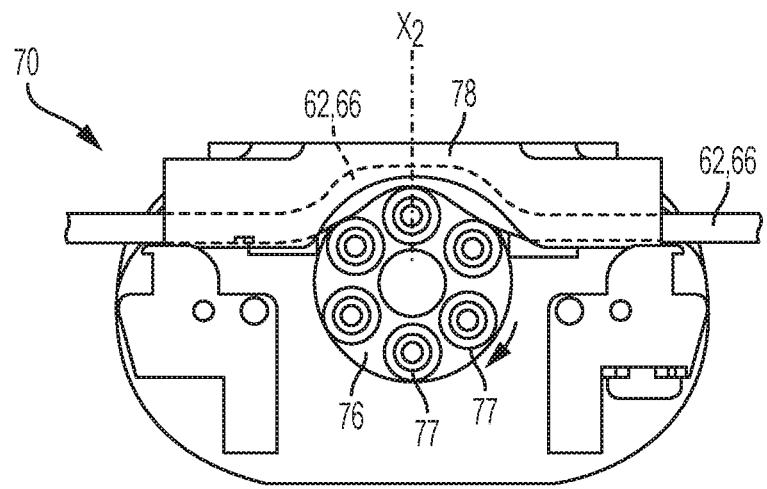
Figure 8D:
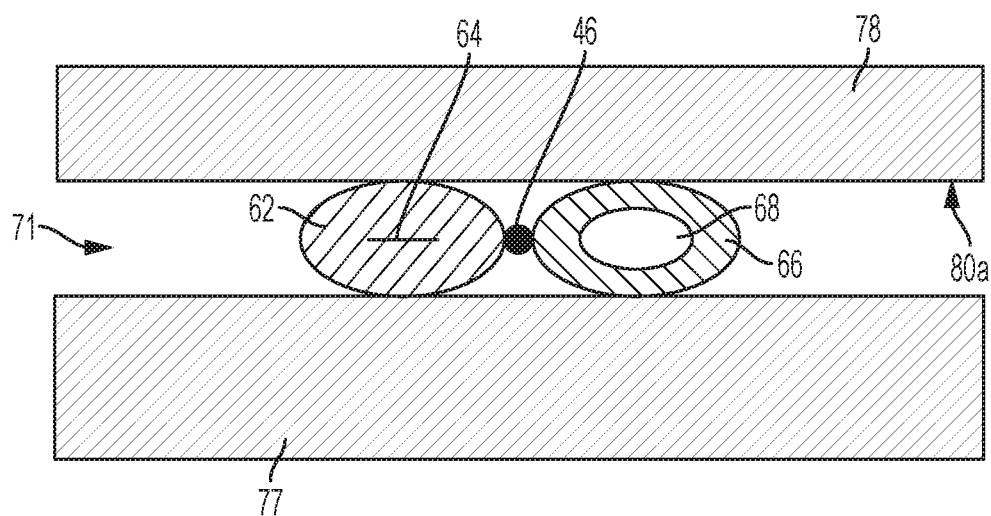

Referring to the side cross-sectional view of FIG. 8A, the pump head 70 may be moved into a fully closed configuration such that the multi-lumen tubing of FIGS. 4A-B is in direct contact with the roller assembly 76 and the concave bottom portion 80a (FIG. 7B) of the occlusion bed 78. As depicted by the front cross-sectional view of FIG. 8B taken about line $X_1$ (FIG. 8A), the inflow 62 and outflow 66 tubes are disposed within the clearance space 71 between the roller assembly 76 and bottom surface 80a of the occlusion bed 78. One or more rollers 77 of the roller assembly 76 may be in direct contact with the inflow 62 and outflow 66 tubes. Importantly, in the configuration depicted in FIGS. 8A-B, the roller(s) 77 do not substantially compress either of the inflow 62 or outflow 66 tubes, thereby maintaining the respective inflow 64 and outflow 68 lumens in the fully open configuration. Referring to FIG. 8C-D, as the roller assembly 76 rotates (e.g., in a clockwise direction; see arrow) the roller 77 taken about the line $X_2$ moves along and compresses each of the inflow 62 and outflow 66 tubes, which are disposed within the clearance space 71 between the roller assembly 76 and bottom surface 80a of the occlusion bed 78. As one of the rollers 77 rotates in to position directly in line with X2, the clearance space 71 between the roller assembly 76 and the bottom surface 80a of the occlusion bed is reduced causing contact between the roller and the multi-lumen tubing assembly 60. As shown in FIG. 8D, contact pressure from the roller 77 causes the smaller inflow lumen 64 of the inflow tube 62 to completely collapse, thereby pumping cooling fluid from the fluid source to the ablation probe. By contrast, the thinner wall of the outflow tube 66 does not cause the outflow lumen 68 to completely collapse, thereby maintaining a continuously open lumen through which the cooling fluid may return from the ablation probe to the fluid source. As the rollers 77 of the roller assembly 76 repeatedly move along the multi-lumen tubing, the repeated collapsing and re-opening of the inflow lumen 64 pumps cooling fluid throughout the ablation system. Since the outflow lumen 68 never fully collapses, it remains not subjected to the peristaltic effect thereby allowing the cooling fluid to return to the fluid source.

Figure 9A:
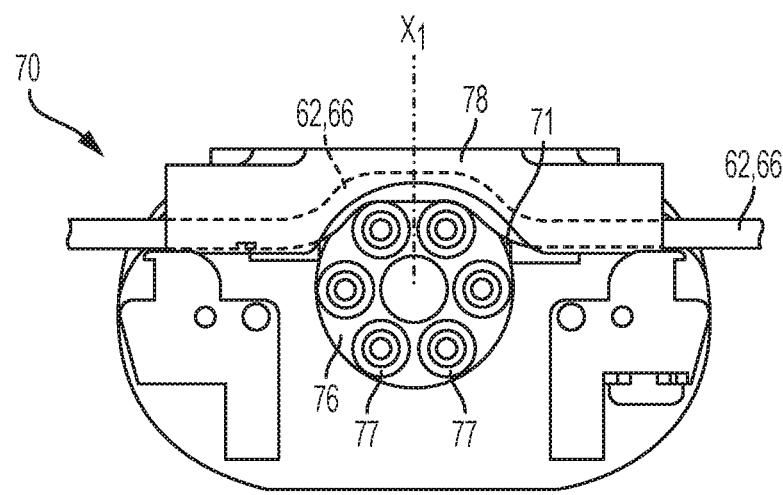
FIGS. 9A-D depict side (FIGS. 9A, 9C) and front (FIGS. 9B, 9D) cross-sectional views of the multi-lumen tubing of FIGS. 5A-B within a pump assembly in a fully closed configuration, according to another embodiment of the present disclosure.

Referring to the side cross-sectional view of FIG. 9A, in another embodiment the pump head 70 may be moved into a fully closed configuration such that the inflow tube 62 of the multi-lumen tubing of FIGS. 5A-B is in direct contact with the roller assembly 76 and the concave bottom portion 80a (FIG. 9B) of the occlusion bed 78. As depicted by the front cross-sectional view of FIG. 9B taken about line $X_1$ (FIG. 9A), the inflow 62 and outflow 66 tubes are disposed within the clearance space 71 between the roller assembly 76 and bottom surface 80a of the occlusion bed 78. One or more rollers 77 of the roller assembly 76 may be in direct contact with the inflow 62 tube but not the smaller diameter outflow tube 66. Importantly, in the configuration depicted in FIGS. 9A-B, the roller(s) 77 do not substantially compress either of the inflow 62 or outflow 66 tubes, thereby maintaining the respective inflow 64 and outflow 68 lumens in the fully open configuration. Referring to FIG. 9C, as the roller assembly 76 rotates (e.g., in a clockwise direction; see arrow) the roller 77 taken about the line $X_2$ moves along and compresses the inflow tubing 62. The roller 77 may contact, but does not substantially compress, the outflow tube 66. As discussed above, the larger outer diameter of the inflow tube 62 causes the inflow lumen 64 to completely collapse, thereby pumping cooling fluid from the fluid source to the ablation probe. By contrast, the smaller outer diameter of the outflow tube 66 does not cause the outflow lumen 68 to completely collapse, thereby maintaining a continuously open lumen through which the cooling fluid may return from the ablation probe to the fluid source. As the rollers 77 of the roller assembly 76 repeatedly move along the multi-lumen tubing, the repeated collapsing and re-opening of the inflow lumen 64 pumps cooling fluid throughout the ablation system. Since the outflow tube 66 is not substantially compressed the outflow lumen 68 remains open thereby allowing the cooling fluid to return to the fluid source.

Figure 9B:
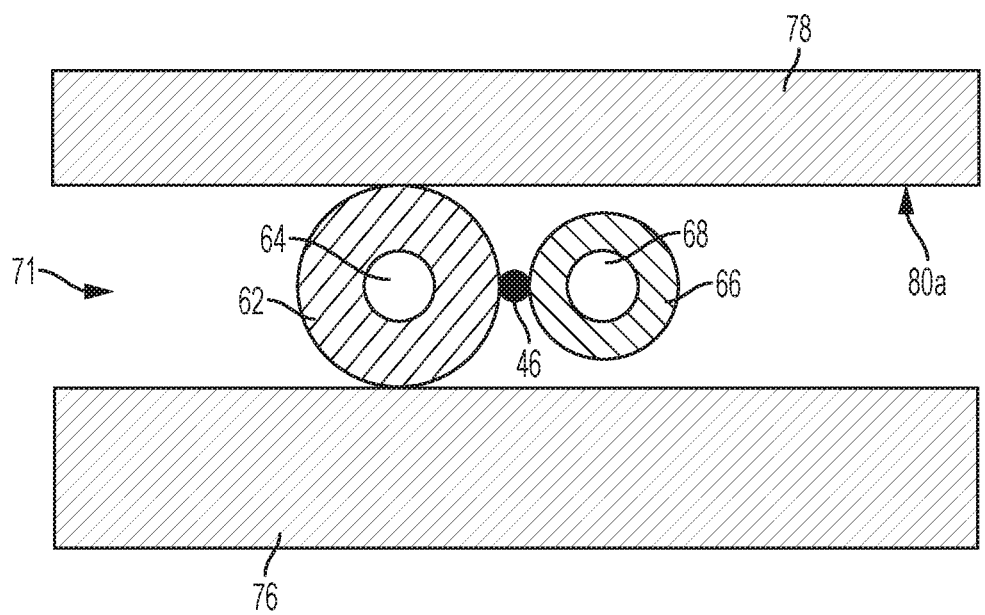
Figure 9C:
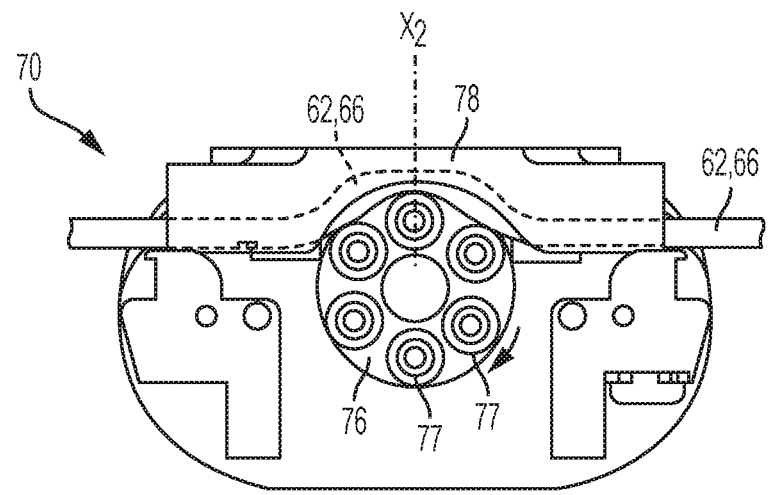
Figure 9D:
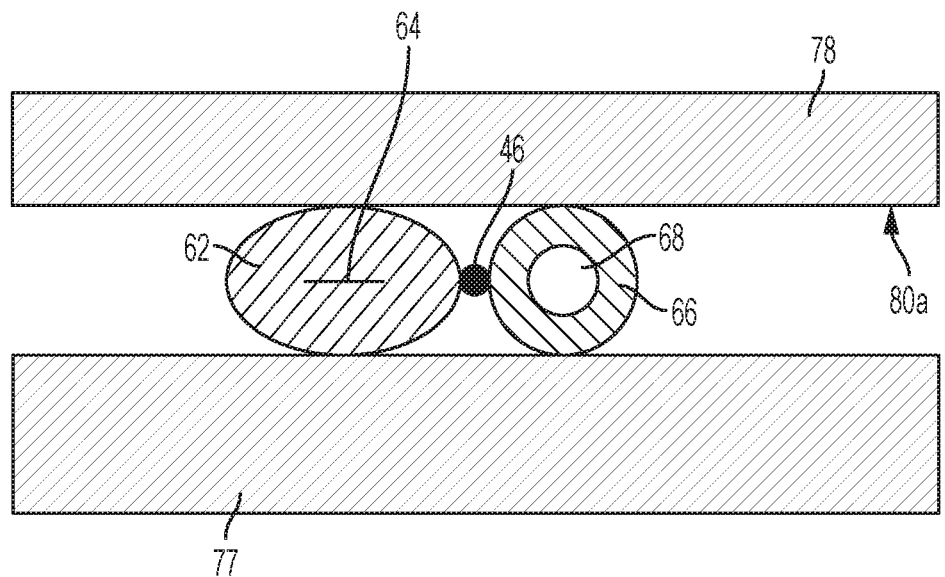
Figure 10:
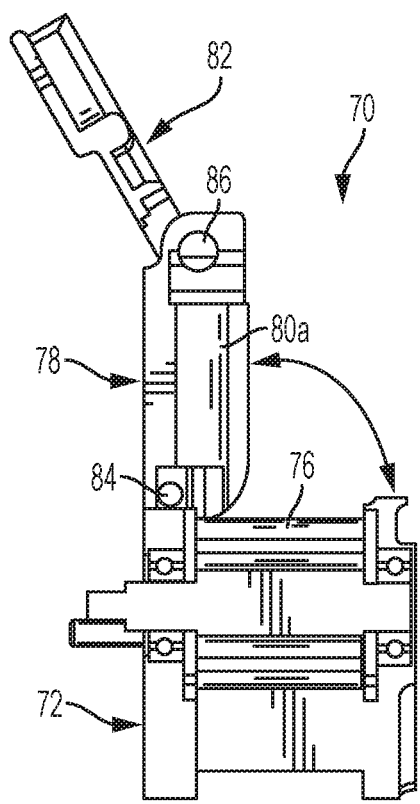
FIG. 10 depicts a side view of a pump assembly in a fully open configuration, according to one embodiment of the present disclosure.
Figure 11:
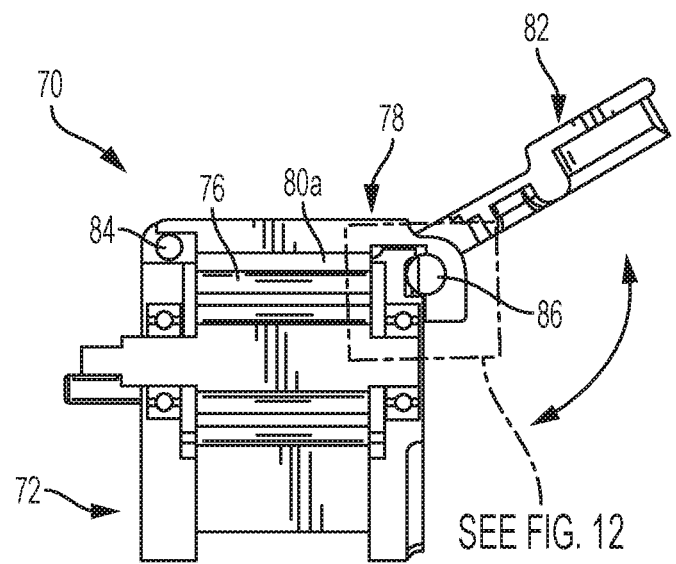
FIG. 11 depicts a side view of a pump assembly in a partially open configuration, according to one embodiment of the present disclosure.

Referring to FIGS. 10 and 11, a side view of the pump head 70 is shown with the occlusion bed 78 being pivotally coupled to the body 72 of the pump head 70 by a first hinge 84, and to the front cover 82 by a second hinge 86. The occlusion bed 78 may rotate approximately 90 degrees about the first hinge 84 to move the pump head 70 from a fully open (FIG. 9) to a partially closed (FIG. 10) configuration. In the partially closed configuration the concave portion 80a of the occlusion bed 78 encloses the corresponding convex profile of the roller assembly 76, but the front cover 82 remains in an open configuration.

Referring to FIG. 11, the second hinge 86 includes an anti-swing mechanism that prevents the front cover 82 from being moved to a fully closed configuration until after the occlusion bed 78 is positioned above the roller assembly 76. As depicted in the enlarged view of FIG. 12, the anti-swing mechanism includes a piston 88 slidably disposed within a first cavity 81 on the planar bottom portion 80a of the occlusion bed 78. The top surface 98 of the piston 88 includes a second cavity 89 configured to receive a compression spring 92. As will be understood by those of skill in the art, the compression spring 92 includes an unconstrained length (not shown) that exceeds the length of the second cavity 89. The compression spring 92 is disposed within the second cavity 89 of the piston 88 in a partially constrained configuration such that the first end 94 of the compression spring 92 presses against an upper portion 79 of the occlusion bed 78 and the second end 96 of the compression spring 92 presses against an inner surface 89a of the piston 88 defined by the second cavity 89. The force applied by the partially constrained compression spring 92 urges the piston 88 to slide within the first cavity 81 such that a tab 90 on the bottom surface 99 of the piston 88 extends beyond the planar bottom portion 80a of the occlusion bed 78. When the occlusion bed 78 and front cover 82 are in the fully or partially open configuration, the piston 88 is retained within the first cavity 81 by a finger-like projection 91 (e.g., lip, edge, hook etc.) that includes a substantially planar bottom surface 91a configured to engage a corresponding planar surface 86a of the second hinge 86. The opposing planar surfaces 91a, 86a serve as a locking mechanism that prevents the front cover 82 from pivoting about the second hinge 86. The locking mechanism also retains the piston 88 within the first cavity 81 such that only the tab 90 extends beyond the planar bottom surface 80a of the occlusion bed 78.

Figure 12:
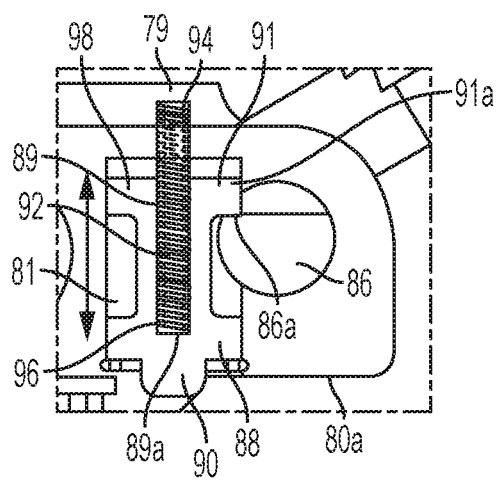
FIG. 12 depicts a side view of the anti-swing mechanism of FIG. 11B in an unlocked configuration, according to another embodiment of the present disclosure.
Figure 13:
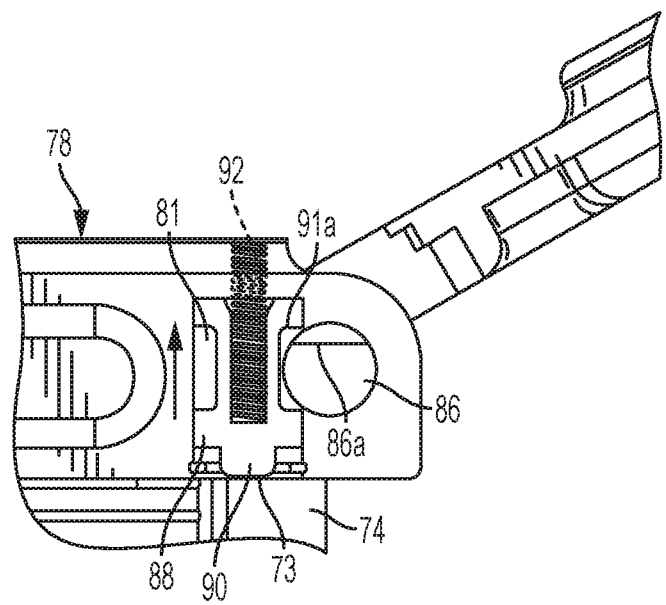
FIG. 13 depicts a side view of the pump assembly in a partially closed configuration, according to one embodiment of the present disclosure.
Figure 14:
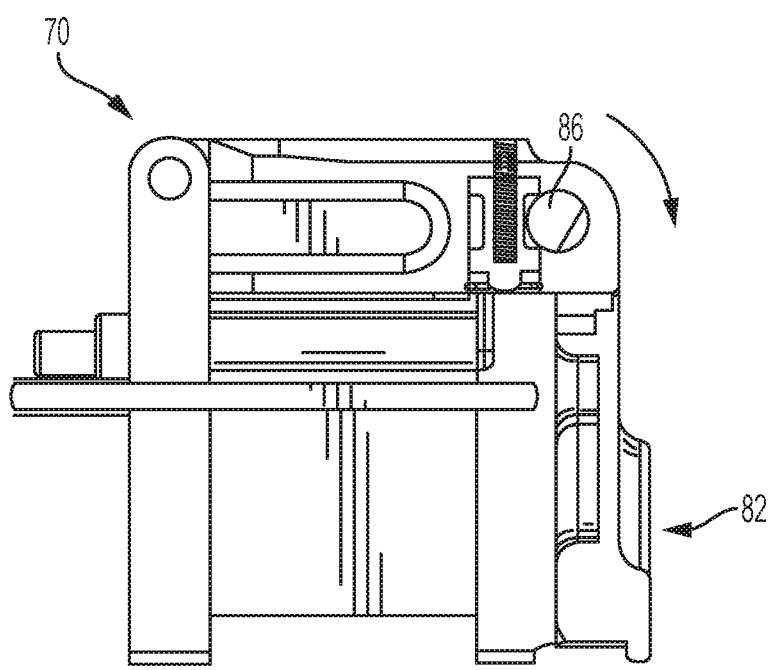
FIG. 14 depicts a side view of the pump assembly in a fully closed configuration, according to one embodiment of the present disclosure.
Figure 15:
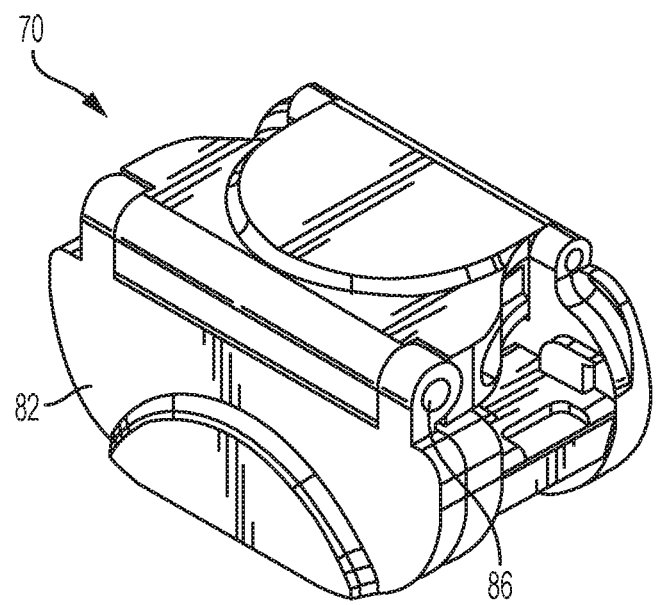
FIG. 15 depicts an isometric view of the pump assembly in a fully closed configuration, according to one embodiment of the present disclosure.

Referring to FIG. 12, as the occlusion bed 78 is lowered into position over the roller assembly, the tab 90 of piston 88 contacts a top surface 73 of the face plate 74. The downward force exerted against the tab 90 forces the piston 88 to slide into the first cavity 81 as the compression spring 92 moves into a more constrained configuration. As the piston 88 slides into the first cavity 81, the planar bottom surface 91a of the finger-like projection 91 disengages the corresponding planar surface 86a of the second hinge 86. As depicted in the cross-sectional (FIG. 13) and isometric (FIG. 14) views, the front cover 82 may rotate at least approximately 90 degrees about the unlocked second hinge 86 to place the pump head 70 in a fully closed configuration.

As discussed above, peristaltic tubing is designed to compress to the point that the lumen of the inflow tube completely collapses/closes every time a roller passes over its surface. The elastic nature of the peristaltic tubing allows the lumen to re-open as the roller moves off its surface. The repeated collapsing and re-opening creates pressure within the inflow lumen that forces the cooling fluid to flow from the fluid source to the fluid-cooled ablation probe. The cooling fluid then returns to the fluid source for re-cooling and re-circulation through an outflow lumen. The fluid flow rate through the multi-lumen tubing may be controlled by varying the rate at which the roller assembly rotates. Because the multiple-use subassembly is configured for use with infusion and fluid-cooled ablation systems, the pump motor is configured to drive rotation of the pump connection at speeds capable of generating fluid flow rates ranging from 0.05 ml/min to 100 ml/min.

Infusion ablation systems typically deliver infusion fluid (e.g., sterile saline) to the tissue ablation site at rate of approximately 0.05-0.7 ml/min. Single-lumen peristaltic tubing may be used to deliver the infusion fluid to the ablation probe because there is no need to circulate cooling fluid throughout the system. Although multi-lumen tubing is not required to circulate cooling fluid, infusion ablation systems may still include multiple-lumen peristaltic tubing. For example, infusion ablation probes may include five (or more) infusion tines, with each tine having a dedicated inflow lumen. An advantage of the integrated pump head disclosed herein is the ability of the easy-to-load layout to accept various tubing arrangements across the roller assembly prior to closing the occlusion bed. For example, the dedicated inflow lumens for each of the five separate infusion tines may include multiple tubes attached in a side-by-side configuration for placement across the roller assembly as a single multi-tube unit. Alternatively, the dedicated inflow lumens for each infusion tine may include individual tubes that are placed next to each other across the roller assembly prior to closing the occlusion bed. In one embodiment, the ability of the integrated pump head to receive various tubing configurations may allow the multiple-use subassembly to perform multiple infusion and/or ablation procedures simultaneously.

Figure 16:
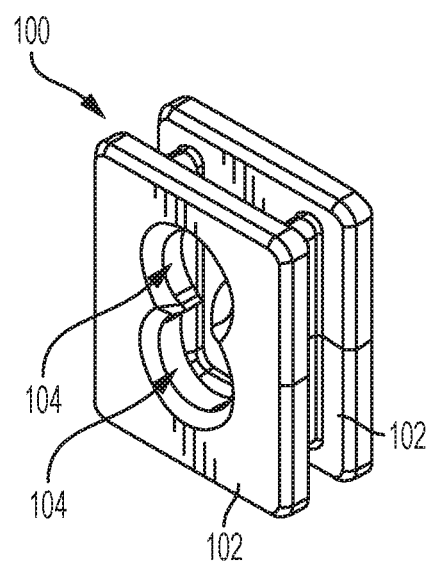
FIG. 16 depicts an isometric view of a pump clip configured to engage the outer surface of the multi-lumen tubing, according to yet another embodiment of the present disclosure.
Figure 17:
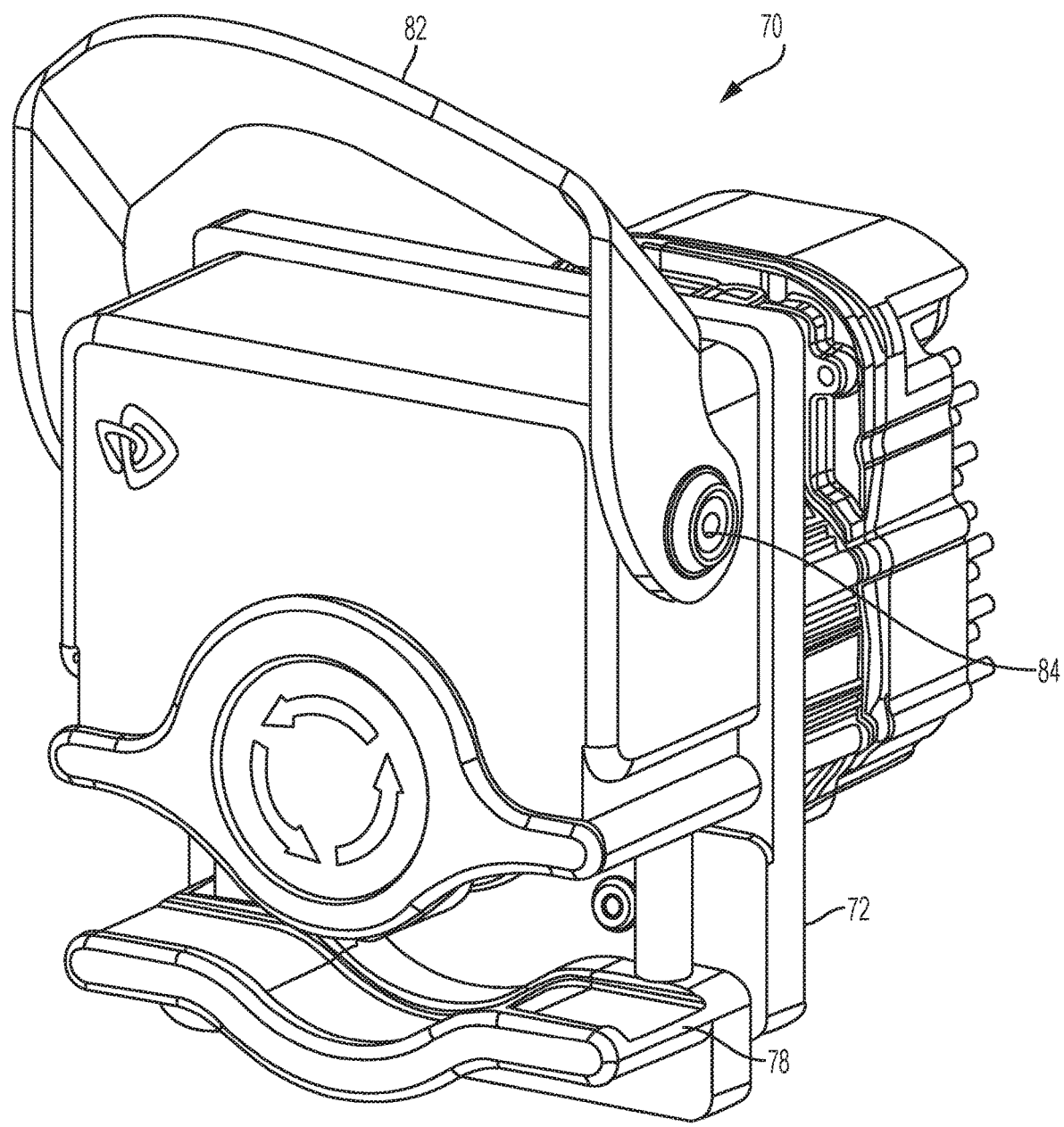
FIGS. 17-18 depict another embodiment of an improved peristaltic pump design.
Figure 18:
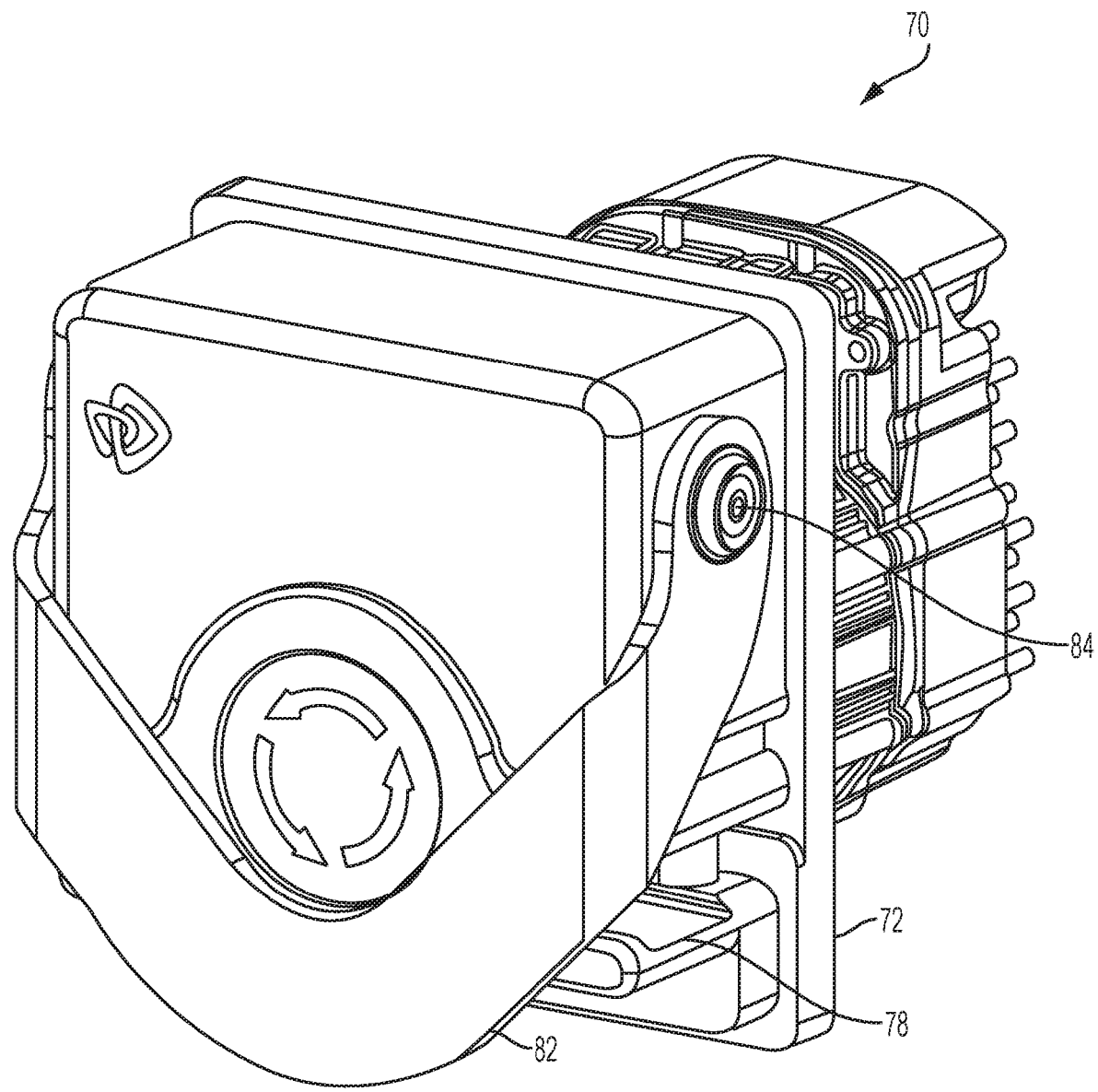
Figure 19:
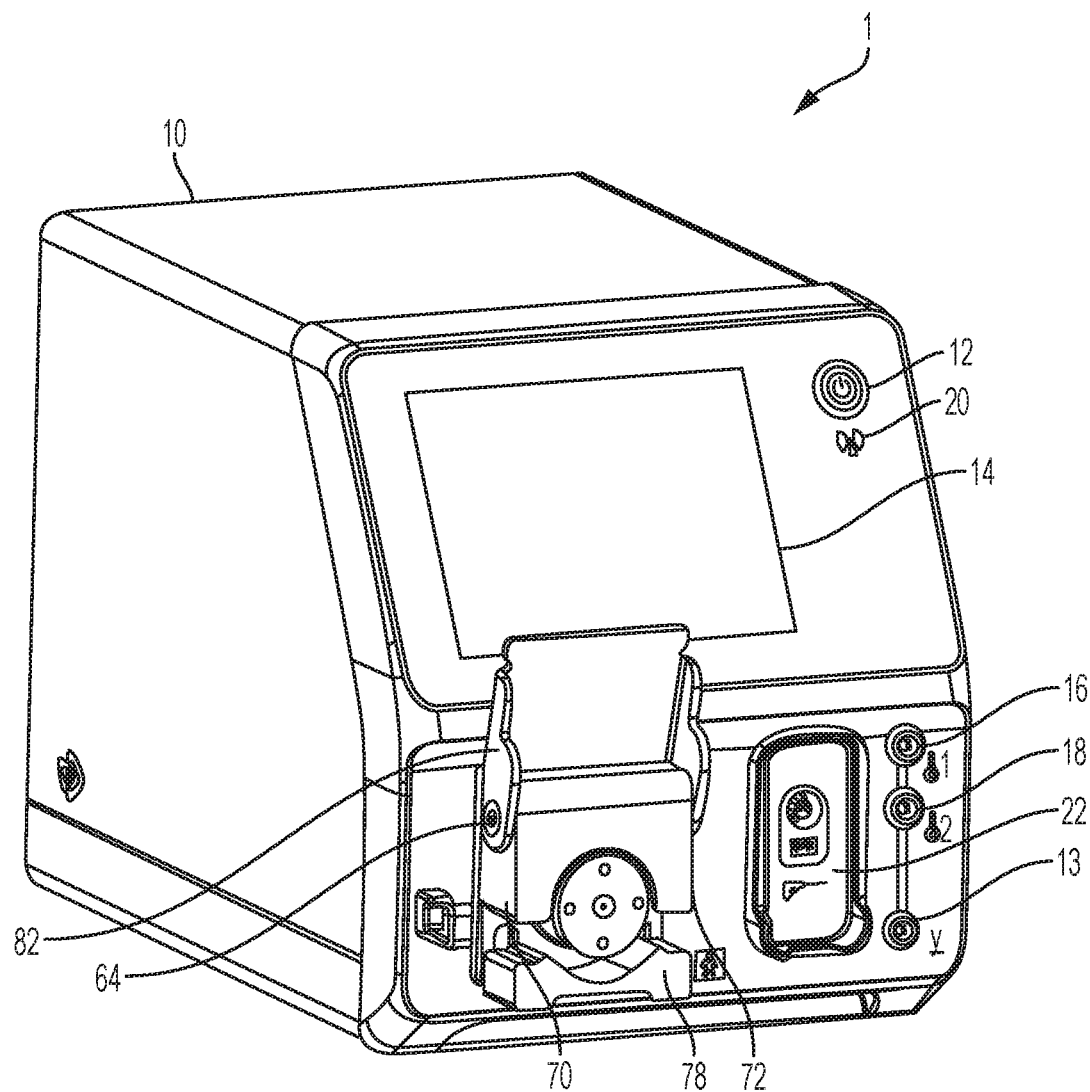
FIGS. 19-20 depict a front view of a multiple-use subassembly, according to one embodiment of the present disclosure.
Figure 20:
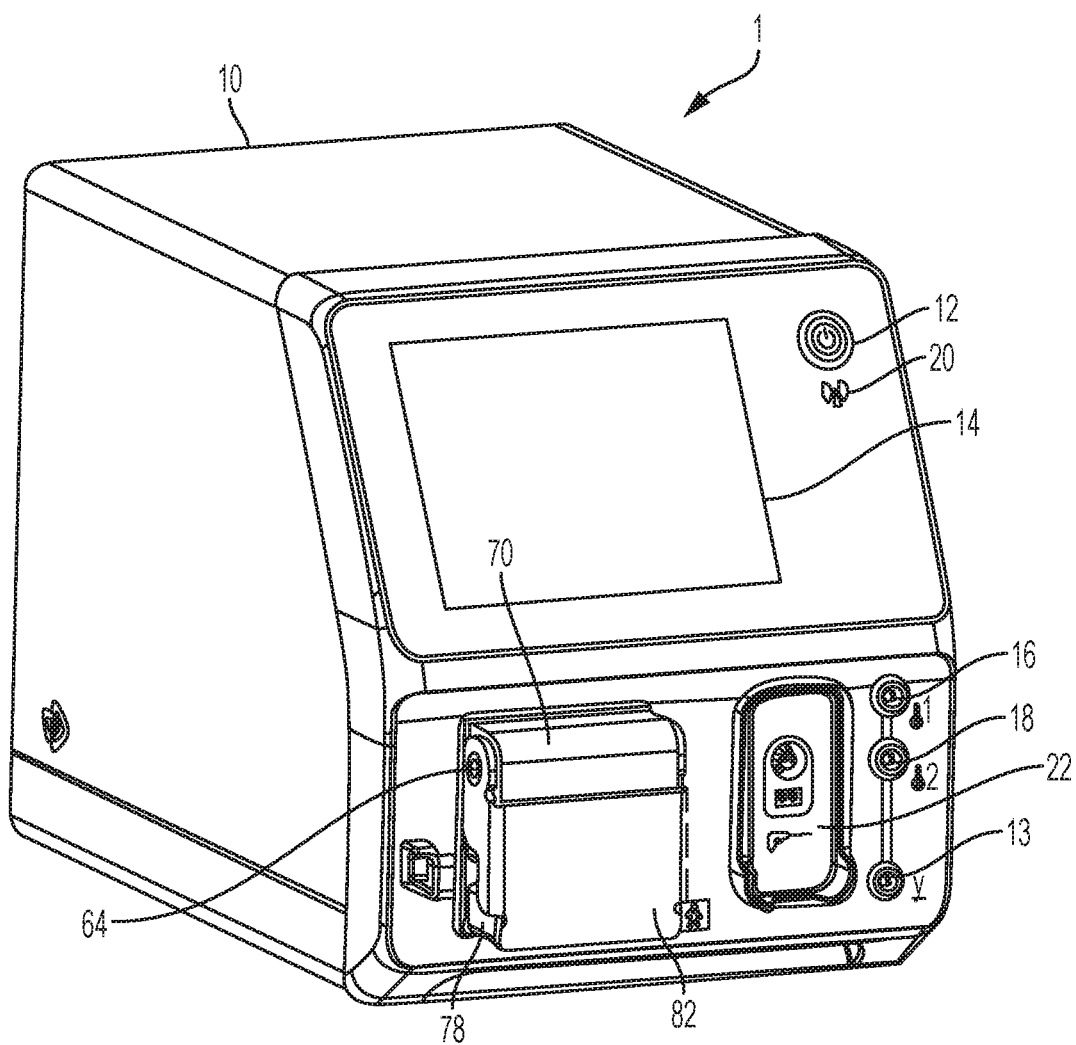

Referring again to FIG. 8B and/or FIG. 9B, a clearance space 71 of approximately 0.1-0.2 inches is created between the roller assembly 76 and bottom surface 80a of the occlusion bed 78 when the pump head is in the fully closed configuration. As the roller assembly 76 rotates it generates a "pulling" force that tends to draw the multi-lumen tubing through the clearance space 71 in the direction of rotation (i.e., towards the ablation probe). To prevent the tubing from moving (i.e., sliding) within the clearance space 71, and potentially disrupting the procedure and/or harming the patient, the multiple-use subassembly may further include a pump clip that engages (i.e., locks onto) the outer surface of the tubing adjacent to the pump head. Referring to FIG. 16, in one embodiment a dual-lumen pump clip 100 may include opposing planar elements 102 with corresponding apertures 104 configured to receive and frictionally engage the outer surface of the multi-lumen tubing. As shown in FIG. 1, the pump clip 100 may be disposed about a portion of the multi-lumen tubing that extends immediately between the pump head and the fluid source (not shown). As the roller assembly rotates, the multi-lumen tubing is pulled in a distal direction, e.g., towards the patient. The pump clip 100 includes a thickness that exceeds that clearance space 71 between the roller assembly and occlusion bed (e.g., greater than 0.2 inches), and therefore serves as a stopping mechanism that prevents the multi-lumen tubing from being drawn through the pump head during the ablation procedure. Other embodiments of the pump clip 100 may be designed to accommodate other tubing configurations such as single or multiple lumen tubing.

Compared to conventional systems, the multiple-use subassembly described herein includes a small footprint that takes up less space in the procedure room and supports all infusion and fluid-cooled ablation systems. Unlike conventional pump heads that include restricted openings and/or special routing paths, the integrated pump head 70 includes an easy-to-load layout that readily accepts a variety of single and multi-lumen tube designs. The unique multi-lumen tubing 60 design eliminates the need for the user to remain cognizant of which tube is the inflow tube 62 or outflow tube 66 when placing the tubing within the pump head. The spring-loaded front cover 82 and the locking-cam action (FIGS. 9-13) also generates a significant amount of compression force on the relatively hard, multi-lumen tubing 60 with little input force from the end user. Taken together, the easy-to-load layout of the pump head 70 and multi-lumen tubing 60 provide superior performance and ease-of-use, which decreases preparation time and minimizes user error during setup and use.

Referring to FIGS. 17-20, another embodiment of the pump head is shown. This pump head design is intended to work with either single or multiple lumen peristaltic pump tubing, such as the innovative tubing described above. Key features of this new pump design include, solid pump rollers to compress the tubing, self-locking handle that hinges to open and close the bottom-loading occlusion bed, wide opening when occlusion bed 78 is in the open position for easy loading of the tubing onto the occlusion bed 78, a high torque precision speed direct drive motor 24 with integrated motor controller, and an integrated sensor to detect the status of the pump door in either an open or closed position. Advantages of this new pump head design include increased longevity, reduced noise, high speed operation, improved occlusion bed opening and closing.

This pump is designed with solid rollers which omit the typical rollers supported on ball bearings that are commonly found in the art. Such solid rollers will improve reliability and reduce the noise of the pump 70 during use. Another advantage of using solid rollers is longevity of the rollers and the ball bearings for the rollers. The increase in longevity will decrease the amount of maintenance of the pump, giving more time and money to the operator. The pump 70 may also have a self-locking handle to open and close the occlusion bed 78 mechanism. This handle may hinge relative to the pump 70 in an up and down, or an in and out direction. The handle provides the user with an ease of use during the operation of loading and unloading the tubing. Commonly known pumps in the art require precise placement of tubing and are often difficult to load, requiring the user to spend additional procedure time with the patient. By providing an easy to use handle that automatically raises and lowers the occlusion bed 78 away from the rollers this will increase ease of set-up and use and also reduce overall procedure time.

Additionally, the occlusion bed 78 of this pump design may be supported by linear brushings that results in a simple design with few moving parts to increase the reliability and cost effectiveness of the pump design. The occlusion bed 78 may also be grooved to support axisymmetric multi-lumen tubing lateral motion. Axial tracking of dual lumen tubing may lead to pinching and or binding of the dual lumen tube into the rollers, resulting in high wear and/or failure of the tubing material or even stalling of the pump motor. By creating a grooved support in the occlusion bed 78 to reduce this axial tracking such concerns may be alleviated.

The pump design may also include a rotor assembly that is a direct drive using a servo motor to create a high-torque, low speed pumping mechanism. Such a design will advantageously remove the need for a gear box or a high-speed motor, allowing lower speed operation for a lower, more precise flow rates and quieter operation. Additionally, the motor may be used with an integrated onboard motor controller/driver to enable programmable motor functions, such as ramp up/down, motor actuation profiles, precision speed control. This integrated motor controller/drive may be able to created unique flow rate schemes and/or maintain precision flow rates. The motor controller/drive may be integrated into the capital equipment used in conjunction with the pump 70, such as a device with bi-directional communication of inputs and outputs. Additionally, a stepper motor could also be used with the integrated controller/driver. The stepper motor would similarly be able to provide a high-torque, low speed solution.

This pump 70 design may also include integrated sensors. Such sensors may be used to provide the user and system with key information, such as when the occlusion bed 78 is open or closed. Additionally, a flow sensor 120 can be added to the pump design to detect the flow rate of the fluid through the tubing, if there is air in the system, if priming is requiring, or if there is any axial tracking of the dual lumen tubing 60. The flow sensor 120 can be integrated into the system in several different ways. The flow sensor 120 could be placed solely in fluid communication with the inflow tubing 62, giving the user accurate flow rates of fluid that is entering the patient or probe 42, depending on the type of probe 42 being used in conjunction with the system. In another variation, the flow sensor 120 could be placed solely in fluid communication with the outflow tubing 66, giving the user accurate flow rates of fluid that is leaving the patient or probe 42, depending on the type of probe 42 being used in conjunction with the system. Finally, there could be a flow sensor 120 placed in fluid communication with both the inflow tubing 62 and the outflow tubing 66. This variation is beneficial because it gives the user much more information in terms of flow rate. The user would now know the flow rate of fluid going into the patient or probe 42, as well as the flow rate leaving the patient or probe 42. Additionally, the user could get an accurate measurement of the flow rate of fluid that was actually delivered to the patient by subtracting the flow rate from the outflow tubing 66 from the flow rate of the inflow tubing 62.

All of the systems, assemblies and/or methods disclosed and claimed herein can be made and executed without undue experimentation in light of the present disclosure. While the present disclosure has been described in terms of preferred embodiments, it will be apparent to those of skill in the art that variations can be applied to the systems, assemblies and/or methods described herein without departing from the concept, spirit and scope of the disclosure. All such similar substitutes and modifications apparent to those skilled in the art are deemed to be within the spirit, scope and concept of the disclosure as defined by the appended claims.

While embodiments of the disclosure have been illustrated and described, it is not intended that these embodiments illustrate and describe all possible forms of the disclosure. Rather, the words used in the specification are words of description rather than limitation, and it is understood that various changes may be made without departing from the spirit and scope of the disclosure.

What is claimed is:

1. A system for ablating a treatment site, comprising:
   a multiple-use subassembly comprising:
   a housing;
   an energy source;
   a pump motor;
   a pump head connected to the pump motor, the pump head having an occlusion bed and roller assembly;
   an ablation probe connected to the energy source; and
   a fluid source configured to be connected to the ablation probe by a multi-lumen tubing; and
   wherein the multi-lumen tubing further comprises an inflow lumen and an outflow lumen, wherein the inflow lumen is configured to at least partially close when compressed by a roller of the roller assembly and the outflow lumen is configured to remain open when compressed by a roller of the roller assembly.

2. The system of claim 1, wherein the occlusion bed is configured to be pivotally coupled to the pump head.

3. The system of claim 2, wherein the pump motor is configured to move the roller.

4. The system of claim 2, wherein the fluid source includes a cooling fluid.

5. The system of claim 2, wherein the fluid source includes an electrically conductive fluid.

6. The system of claim 2, wherein a cooling fluid is configured to flow from the fluid source to the ablation probe through the inflow lumen and is configured to return to the fluid source through the outflow lumen.

7. The system of claim 6, wherein the fluid is configured to flow through the multi-lumen tubing at a flow rate of at least 80 ml/min.

8. The system of claim 2, wherein a fluid is configured to flow from the fluid source to the ablation probe through the inflow lumen.

9. The system of claim 8, wherein the fluid is configured to flow through the inflow lumen at a flow rate of approximately 0.05 ml/min to approximately 0.7 ml/min.

10. The system of claim 1, wherein the energy source is capable of generating radiofrequency energy, microwave energy or electroporation energy.

11. The system of claim 1, wherein the multi-lumen tubing further comprises an outflow tube and an inflow tube, wherein the inflow tube is configured to be made from a softer durometer material than the outflow tube.

12. A system for ablating a treatment site, comprising:
    a multiple-use subassembly comprising a housing and a pump head; wherein the pump head comprises an occlusion bed and a roller;
    an ablation probe;
    a fluid source configured to be connected to the ablation probe by an inflow lumen and an outflow lumen;
    wherein the inflow lumen is configured to at least partially close when compressed by the roller and the outflow lumen is configured to remain open when compressed by the roller.

13. The system of claim 12, further comprising an energy source.

14. The system of claim 13, wherein the energy source is capable of generating radiofrequency energy, microwave energy or electroporation energy.

15. The system of claim 13, wherein the occlusion bed is configured to be pivotally coupled to the pump head.

16. A system for ablating tissue, comprising:
    a multiple-use subassembly comprising a housing and a pump head; wherein the pump head comprises an occlusion bed and at least one roller;
    an ablation probe;
    a fluid source fluidly configured to be connected to the ablation probe by an inflow lumen and an outflow lumen;
    wherein the inflow lumen is configured to at least partially close when compressed by the at least one roller and the outflow lumen is configured to remain open when compressed by the at least one roller.

17. The system of claim 16, further comprising an energy source.

18. The system of claim 17, wherein the energy source is capable of generating radiofrequency energy, microwave energy or electroporation energy.

19. The system of claim 16, wherein the pump head comprises up to nine rollers.

20. The system of claim 16, wherein the occlusion bed is configured to be pivotally coupled to the pump head.

\* \* \* \* \*